(12) United States Patent
Rogers

(10) Patent No.: US 10,874,543 B2
(45) Date of Patent: *Dec. 29, 2020

(54) DEVICES FOR VESTIBULAR OR CRANIAL NERVE STIMULATION

(71) Applicant: Scion Neurostim, LLC, Raleigh, NC (US)

(72) Inventor: Lesco L. Rogers, Raleigh, NC (US)

(73) Assignee: Scion Neurostim, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/864,527

(22) Filed: Jan. 8, 2018

(65) Prior Publication Data

US 2019/0201234 A1    Jul. 4, 2019

Related U.S. Application Data

(63) Continuation of application No. 14/251,860, filed on Apr. 14, 2014, now Pat. No. 9,861,518, and a continuation-in-part of application No. 12/669,684, filed on Apr. 19, 2010, now Pat. No. 8,262,717, and a continuation of application No. 12/704,872, filed on Feb. 12, 2010, now Pat. No. 8,696,724, and a continuation of application No. 12/699,374, filed on
(Continued)

(51) Int. Cl.
*A61F 7/00* (2006.01)
*A61F 7/12* (2006.01)
*A61F 7/02* (2006.01)
*A61N 1/32* (2006.01)

(52) U.S. Cl.
CPC .............. *A61F 7/00* (2013.01); *A61F 7/007* (2013.01); *A61F 7/12* (2013.01); *A61F 2007/0075* (2013.01); *A61F 2007/0296* (2013.01); *A61N 1/32* (2013.01)

(58) Field of Classification Search
CPC .......................... A61F 7/12; A61F 2007/0075
See application file for complete search history.

(56) References Cited

U.S. PATENT DOCUMENTS

| 4,117,881 A | 10/1978 | Williams et al. |
| 4,244,377 A | 1/1981 | Grams |

(Continued)

FOREIGN PATENT DOCUMENTS

| DE | 10065592 | 7/2002 |
| JP | H08195997 | 7/1996 |

(Continued)

OTHER PUBLICATIONS

Baier et al., "Evidence for Modulation of Opioidergic Activity in Central Vestibular Processing: A [18F] Diprenorphine PET Study", Human Brain Mapping, 2010, 31: 550-555.
(Continued)

*Primary Examiner* — Kaitlyn E Smith
(74) *Attorney, Agent, or Firm* — Myers Bigel, P.A.

(57) ABSTRACT

A nerve tissue stimulator configured for contacting to or insertion in the body of a subject to stimulate a tissue therein, said probe comprising: (a) a support configured for contacting to or positioning adjacent a tissue of said subject; (b) at least one thermoelectric device (TED) on said support and positioned for thermally stimulating said nerve tissue.

21 Claims, 12 Drawing Sheets

Related U.S. Application Data

Feb. 3, 2010, now Pat. No. 8,267,984, and a continuation of application No. 12/693,016, filed on Jan. 25, 2010, now Pat. No. 8,267,983, which is a continuation-in-part of application No. 12/166,953, filed on Jul. 2, 2008, now abandoned, which is a continuation-in-part of application No. 11/972,267, filed as application No. PCT/US2008/071935 on Aug. 1, 2008, now abandoned.

(60) Provisional application No. 61/224,668, filed on Jul. 10, 2009, provisional application No. 60/953,700, filed on Aug. 3, 2007, provisional application No. 60/908,261, filed on Mar. 27, 2007, provisional application No. 60/884,546, filed on Jan. 11, 2007.

(56) References Cited

U.S. PATENT DOCUMENTS

| | | | |
|---|---|---|---|
| 4,585,002 | A * | 4/1986 | Kissin .................. A61F 5/00 607/96 |
| 4,860,748 | A | 8/1989 | Chiurco et al. |
| 4,918,757 | A | 4/1990 | Janssen et al. |
| 5,097,828 | A | 3/1992 | Deutsch |
| 5,215,086 | A | 6/1993 | Terry, Jr. et al. |
| 5,298,692 | A | 3/1994 | Ikeda et al. |
| 5,367,890 | A | 11/1994 | Doke |
| 5,376,184 | A | 12/1994 | Aspden |
| 5,419,780 | A | 5/1995 | Suski |
| 5,746,702 | A | 5/1998 | Gelfgat et al. |
| 5,762,612 | A | 6/1998 | Campbell |
| 5,837,929 | A | 11/1998 | Adelman |
| 5,871,526 | A | 2/1999 | Gibbs et al. |
| 6,016,449 | A * | 1/2000 | Fischell ............... A61B 5/0476 607/45 |
| 6,017,337 | A | 1/2000 | Pira |
| 6,055,815 | A | 5/2000 | Peterson |
| 6,094,918 | A | 8/2000 | Burbidge et al. |
| 6,143,975 | A | 11/2000 | Liao et al. |
| 6,165,173 | A | 12/2000 | Kamdar et al. |
| 6,300,150 | B1 | 10/2001 | Venkatasubramanian |
| 6,334,311 | B1 | 1/2002 | Kim et al. |
| 6,511,437 | B1 | 1/2003 | Nakamura et al. |
| 6,746,474 | B2 | 6/2004 | Saadat |
| 6,755,026 | B2 | 6/2004 | Wallach |
| 6,817,191 | B2 | 11/2004 | Watanabe |
| 6,875,196 | B2 | 4/2005 | Abita et al. |
| 6,882,881 | B1 | 4/2005 | Lesser et al. |
| 6,909,917 | B2 | 6/2005 | Woods et al. |
| 6,921,195 | B2 | 7/2005 | Pipe et al. |
| 6,981,381 | B1 | 1/2006 | Wang et al. |
| 7,082,772 | B2 | 8/2006 | Welch |
| 7,164,077 | B2 | 1/2007 | Venkatasubramanian |
| 7,189,252 | B2 | 3/2007 | Krueger |
| 7,234,735 | B2 | 6/2007 | Harada |
| 7,761,168 | B2 | 7/2010 | Gross |
| 7,856,275 | B1 | 12/2010 | Paul et al. |
| 8,083,786 | B2 | 12/2011 | Gafni et al. |
| 8,262,717 | B2 * | 9/2012 | Rogers ................. A61H 39/06 607/113 |
| 8,267,984 | B2 * | 9/2012 | Rogers ................. A61F 7/007 607/113 |
| 8,460,356 | B2 * | 6/2013 | Rogers ................. A61F 7/007 607/113 |
| 8,603,152 | B2 * | 12/2013 | Smith ................... A61F 7/007 607/113 |
| 8,696,724 | B2 * | 4/2014 | Rogers ................. A61F 7/007 607/96 |
| 9,283,111 | B2 * | 3/2016 | Rogers ................. A61F 7/007 |
| 9,849,026 | B2 * | 12/2017 | Rogers ................. A61F 7/007 |
| 9,913,749 | B2 * | 3/2018 | Rogers ................. A61F 7/007 |
| 9,993,366 | B2 * | 6/2018 | Smith ................... A61F 7/007 |
| 2002/0072781 | A1 | 6/2002 | Lattner et al. |
| 2002/0104318 | A1 | 8/2002 | Jaafar et al. |
| 2002/0121094 | A1 | 9/2002 | Vanhoudt |
| 2003/0010006 | A1 | 1/2003 | Swart et al. |
| 2003/0097845 | A1 | 5/2003 | Saunders et al. |
| 2003/0099279 | A1 | 5/2003 | Venkatasubramanian et al. |
| 2003/0158589 | A1 | 8/2003 | Katsnelson |
| 2003/0195588 | A1 * | 10/2003 | Fischell ................ A61N 2/02 607/55 |
| 2004/0102525 | A1 | 5/2004 | Kozachuk |
| 2004/0181269 | A1 | 9/2004 | Lee |
| 2005/0107682 | A1 | 5/2005 | Rao et al. |
| 2005/0145273 | A1 | 7/2005 | Atwood et al. |
| 2005/0165460 | A1 | 7/2005 | Erfan |
| 2005/0203505 | A1 | 9/2005 | Megerman et al. |
| 2006/0082971 | A1 | 4/2006 | Artman et al. |
| 2006/0086118 | A1 | 4/2006 | Venkatasubramanian et al. |
| 2006/0095088 | A1 | 5/2006 | De Ridder |
| 2006/0289050 | A1 | 12/2006 | Alley et al. |
| 2006/0289052 | A1 | 12/2006 | O'Quinn et al. |
| 2006/0293732 | A1 | 12/2006 | Collins et al. |
| 2007/0028956 | A1 | 2/2007 | Venkatasubramanian et al. |
| 2007/0083097 | A1 | 4/2007 | Fujiwara et al. |
| 2007/0087780 | A1 | 4/2007 | Nassimi |
| 2007/0089773 | A1 | 4/2007 | Koester et al. |
| 2007/0135880 | A1 | 6/2007 | Eggers et al. |
| 2007/0167985 | A1 | 7/2007 | Kirby |
| 2007/0198063 | A1 | 8/2007 | Hunter et al. |
| 2007/0203539 | A1 | 8/2007 | Stone et al. |
| 2007/0215194 | A1 | 9/2007 | Bharathan et al. |
| 2007/0225781 | A1 | 9/2007 | Saadat et al. |
| 2007/0226890 | A1 | 10/2007 | Pflueger |
| 2007/0250119 | A1 | 10/2007 | Tyler et al. |
| 2007/0265524 | A1 | 11/2007 | Eda et al. |
| 2008/0015667 | A1 | 1/2008 | Gross |
| 2008/0087316 | A1 | 4/2008 | Inaba et al. |
| 2008/0097549 | A1 | 4/2008 | Colbaugh et al. |
| 2008/0154334 | A1 | 6/2008 | Gavronsky |
| 2008/0168775 | A1 | 7/2008 | Windheim et al. |
| 2008/0182399 | A1 | 7/2008 | Cho |
| 2008/0264464 | A1 | 10/2008 | Lee et al. |
| 2009/0082831 | A1 | 3/2009 | Paul et al. |
| 2009/0182399 | A1 * | 7/2009 | Sylvestre ............. A61F 7/12 607/99 |
| 2010/0198204 | A1 | 8/2010 | Rogers et al. |
| 2010/0198282 | A1 | 8/2010 | Rogers |
| 2010/0198318 | A1 | 8/2010 | Rogers |
| 2010/0211142 | A1 | 8/2010 | Rogers et al. |
| 2011/0313498 | A1 | 12/2011 | Rogers et al. |
| 2011/0313499 | A1 | 12/2011 | Smith et al. |
| 2012/0078337 | A1 | 3/2012 | Darley et al. |
| 2012/0316624 | A1 | 12/2012 | Smith et al. |

FOREIGN PATENT DOCUMENTS

| | | |
|---|---|---|
| JP | H09285468 | 11/1997 |
| JP | 2002123456 | 4/2002 |
| JP | 2006102258 | 4/2006 |
| JP | 2007144057 | 6/2007 |
| WO | 2002/064069 | 8/2002 |
| WO | 2005/074463 | 8/2005 |
| WO | 2006/079484 | 8/2006 |
| WO | 2007/051911 | 5/2007 |
| WO | 2009/020862 | 2/2009 |
| WO | 2010/029536 | 3/2010 |
| WO | 2012/083126 | 6/2012 |

OTHER PUBLICATIONS

Been et al., "The use of tDCS and CVS as methods of non-invasive brain stimulation", Brain Research Reviews, 2007, 56: 346-361.

Bense et al., "Preserved visual-vestibular interaction in patients with bilateral vestibular failure", Neurology, 2004, 63: 122-128.

Brookler, Kenneth H., "Simultaneous Bilateral Bithermal Caloric Stimulation in Electronystagmography", The Laryngoscope, 1971, 81(7): 1014-1019.

Coats, Alfred C., "Temperature Effects on the Peripheral Auditory Apparatus", Science, 1965, 150(702): 1481-1483.

(56) References Cited

OTHER PUBLICATIONS

Deutschländer et al., "Sensory System Interactions During Simultaneous Vestibular and Visual Stimulation in PET", Human Brain Mapping, 2002, 16: 92-103.
Dieterich et al., "Functional brain imaging of peripheral and central vestibular disorders", Brain, 2008, 131: 2538-2552.
Ettenberg et al., "A New n-type and Improved p-type Pseudoternary (Bi2Te3)(Sb2Te3) (Sb2Se3) Alloy for Peltier Cooling", 15th International Conference on Thermoelectrics, 1996, IEEE Catalog No. 96TH8169: pp. 52-56.
Examination Report Corresponding to Australian Patent Application No. 2008284042; dated Oct. 9, 2012.
Fasold et al., "Human Vestibular Cortex as Identified with Caloric Stimulation in Functional Magnetic Resonance Imaging", NeuroImage, 2002, 17: 1384-1393.
Ferre et al., "Vestibular modulation of somatosensory perception", European Journal of Neuroscience, 2011, 34: 1337-1344.
Ferre et al., "Vestibular inputs modulate somatosensory cortical processing", Brain Structure and Function, 2012, 217: 859-864.
Fontanazza, Maria, "A Cooler Way to Stop Seizures", Medical Device & Diagnostic Industry Magazine, 2005: pp. 1-2.
International Preliminary Report on Patentability Corresponding to International Application No. PCT/US2010/060764; dated Jun. 28, 2012.
International Preliminary Report on Patentability Corresponding to International Application No. PCT/US2010/060771; dated May 17, 2012.
International Preliminary Report on Patentability Corresponding to International Application No. PCT/US2011/065321; dated Jun. 27, 2013.
International Preliminary Report on Patentability Corresponding to International Application No. PCT/US2011/065328; dated Jun. 27, 2013.
International Preliminary Report on Patentability Corresponding to International Application No. PCT/US2011/065338; dated Jun. 27, 2013.
International Preliminary Report on Patentability Corresponding to International Application No. PCT/US2011/065396; dated Jun. 27, 2013.
International Preliminary Report on Patentability Corresponding to International Application No. PCT/US2011/065456; dated Jun. 27, 2013.
International Search Report and the Written Opinion of the International Searching Authority Corresponding to International Application No. PCT/US2008/071935; dated Jul. 16, 2009.
International Search Report and the Written Opinion of the International Searching Authority Corresponding to International Application No. PCT/US2010/060764; dated Feb. 22, 2011.
International Search Report and the Written Opinion of the International Searching Authority Corresponding to International Application No. PCT/US2010/060771; dated Feb. 22, 2011.
International Search Report and the Written Opinion of the International Searching Authority Corresponding to International Application No. PCT/US2011/065321; dated Mar. 29, 2012.
International Search Report and the Written Opinion of the International Searching Authority Corresponding to International Application No. PCT/US2011/065328; dated Mar. 29, 2012.
International Search Report and the Written Opinion of the International Searching Authority Corresponding to International Application No. PCT/US2011/065338; dated Apr. 20, 2012.
International Search Report and the Written Opinion of the International Searching Authority Corresponding to International Application No. PCT/US2011/065396; dated Apr. 23, 2012.
International Search Report and the Written Opinion of the International Searching Authority Corresponding to International Application No. PCT/US2011/065456; dated Apr. 4, 2012.
Karim et al., "Neuroimaging to detect cortical projection of vestibular response to caloric stimulation in young and older adults using functional near-infrared spectroscopy (fNIRS)", NeuroImage, 2013, 76: 1-10.
Kimm et al., "Vestibular Effects of Electrical Stimulation of the Cochlea", Archives of Otolaryngology, 1979, 105: 175-179.
Klingner et al., "Components of vestibular cortical function", Behavioural Brain Research, 2013, 236: 194-199.
Kolev, Ognyan, "How caloric vestibular irritation influences migraine attacks", Cephalalgia, 1990, 10: 167-169.
Litchfield, Corinne, "Biomedical Device Maker Teams with NASA to Develop Nano-Sized Biothermal Battery", European Medical Device Manufacturer, 2004, http://www.devicelink.com/emdm/archive/04/10/002.html, 2 pages.
Lobel et al., "Functional MRI of Galvanic Vestibular Stimulation", Journal of Neurophysiology, 1998, 80: 2677-2709.
Lopez et al., "The Human Vestibular Cortex Revealed by Coordinate-Based Activation Likelihood Estimation Meta-Analysis", Neuroscience, 2012, 212: 159-179.
Marcelli et al., "Spatio-temporal pattern of vestibular information processing after brief caloric stimulation", European Journal of Radiology, 2009, 70: 312-316.
Mast et al., "Visual mental imagery during caloric vestibular stimulation", Neuropsychologia, 2006, 44(1): 101-109.
Mcgeoch et al., "Post-stroke tactile allodynia and its modulation by vestibular stimulation: a MEG case study", Acta Neurologica Scandinavica, 2009, 119: 404-409.
Miller et al., "Studies of caloric vestibular stimulation: implications for the cognitive neurosciences, the clinical neurosciences and neurophilosophy", Acta Neuropsychiatrica, 2007, 19: 183-203.
Naito et al., "Cortical correlates of vestibulo-ocular reflex modulation: A PET study", Brain, 2003, 126: 1562-1578.
Nextreme, "Breakthroughs: Thermoelectric Generator Converts Waste Heat into Energy", Medical Product Manufacturing News, 2007, http://www.devicelink.com/mpmm/archive/07/10/014.html, 2 pages.
Office Action Corresponding to Japanese Patent Application No. 2010-519241; dated Dec. 7, 2012.
Office Action Corresponding to Japanese Patent Application No. 2010-519241; dated Jul. 9, 2013.
Office Action Corresponding to U.S. Appl. No. 12/704,872; dated Jan. 29, 2013.
Ramachandran et al., "Can vestibular caloric stimulation be used to treat apotemnophilia?", Medical Hypotheses, 2007, 69: 250-252.
Rode et al., "Bilateral vestibular stimulation does not improve visual hemineglect", Neuropsychologia, 2002, 40: 1104-1106.
Snyder et al., "Hot Spot Cooling using Embedded Thermoelectric Coolers", 22nd IEEE SEMI-THERM Symposium, IEEE Catalog No. 1-4244-0154-2, 2006, pp. 135-143.
Soza Ried et al., "Asymmetries of Vestibular Dysfunction in Major Depression", Neuroscience, 2007, 144: 128-134.
Tellurex Corp., "Thermoelectric cooling semiconductor modules available in new configuration", Medical Product Manufacturing News, 1999, http://www.devicelink.com/mpmm/archive/99/04/cover.hmtl, 2 pages.
Venkatasubramanian et al., "Phonon-Blocking Electron-Transmitting Structures", 18th International Conference on Thermoelectrics, 1999, pp. 100-103.
Vitte et al., "Activation of the hippocampal formation by vestibular stimulation: a functional magnetic resonance imaging study", Experimental Brain Research, 1996, 112: 523-526.
Zhang et al., "Change of extracellular ascorbic acid in the brain cortex following ice water vestibular stimulation: an on-line electrochemical detection coupled with in vivo microdialysis sampling for guinea pigs", Chinese Medical Journal, 2008, 121(12): 1120-1125.
Shinji Nishizawa, "Intervals for Successive Caloric Irrigations", Equilibrium Research, Japan Society for Equilibrium Research, 2001, vol. 60, p. 86-92.
Extended European Search Report Corresponding to European Application No. 14163419.6, dated Jan. 8, 2015; 3 Pages.

* cited by examiner

DEVICES FOR VESTIBULAR OR CRANIAL NERVE STIMULATION

RELATED APPLICATIONS

This application is a continuation of U.S. patent application Ser. No. 14/251,860, filed Apr. 14, 2014, and issued as U.S. Pat. No. 9,861,518 on Jan. 9, 2018, which application is a continuation of, U.S. patent application Ser. No. 12/704,872, filed Feb. 12, 2010, which is itself a continuation-in-part of U.S. patent application Ser. No. 12/699,374, filed Feb. 3, 2010, and issued as U.S. Pat. No. 8,267,984 on Sep. 18, 2012, which itself claims priority under 35 U.S.C. § 119(e) to U.S. Provisional Application No. 61/224,668, filed Jul. 10, 2009; Ser. No. 12/669,684, filed Jan. 19, 2010, and issued as U.S. Pat. No. 8,262,717 on Sep. 11, 2012, which itself claims priority under 35 U.S.C. § 120 to PCT Application No. PCT/US2008/071935, filed Aug. 1, 2008 and under 35 U.S.C. § 119(e) to U.S. Provisional Application No. 60/953,700, filed Aug. 3, 2007; and Ser. No. 12/693,016, filed Jan. 25, 2010, and issued as U.S. Pat. No. 8,267,983 on Sep. 18, 2012, which is itself a continuation-in-part of U.S. patent application Ser. No. 12/166,953, filed Jul. 2, 2008, which is itself a continuation-in-part of U.S. patent application Ser. No. 11/972,267, filed Jan. 10, 2008, which claims priority under 35 U.S.C. § 119(e) to U.S. Provisional Application Nos. 60/884,546, filed Jan. 11, 2007 and 60/908,261, filed Mar. 27, 2007, the disclosure of each which is incorporated herein by reference in its entirety.

FIELD OF THE INVENTION

The present invention concerns apparatuses and associated methods useful for delivering stimulation to the nervous system and/or the vestibular system of an individual, thereby inducing physiological changes in the individual and/or treating or diagnosing a disorder or symptom of the individual

BACKGROUND

Caloric vestibular stimulation ("CVS") has long been known as a diagnostic procedure for testing the function of the vestibular system. In the traditional hospital setting, water or air caloric tests are used to assess levels of consciousness during acute or chronic brain injury. The brain injury may be due to head trauma or a central nervous system event such as a stroke. Other brain injuries occur in the presence of metabolic abnormalities (e.g., kidney disease, diabetes), seizures, or toxic levels of controlled substances or alcohol.

More recently, CVS has been applied to other purposes. A general review of some successful experimental uses of CVS is given in Miller and Ngo, *Acta Neuropsychiatrica* 19:183 (2007). Table 1, which is not intended to be exhaustive, highlights several applications of CVS.

TABLE 1

Disorders/symptoms treated experimentally by CVS

| Disorder/Symptom Treated | Reference |
| --- | --- |
| Dizziness | U.S. Patent Application No. 2003/0195588 |
| Elusive sleep | U.S. Pat. No. 6,748,275 |
| Migraine headaches | O. Kolev, Cephalalgia 10:167 (1990) |
| Neurodegenerative disorders | Y. Yamamoto et al., *Ann Neurol.* 58:175 (2005) |
| Parkinson's Disease | Y. Yamamoto et al., *Ann Neurol.* 58:175 (2005) |
| Reduced respiratory function | U.S. Pat. No. 6,748,275 |
| Restricted airway | U.S. Pat. No. 6,748,275 |
| Seasickness/Travel sickness | U.S. Patent Application No. 2003/0195588 |
| Seizure | U.S. Patent Application No. 2003/0195588 |
| Spatial- and verbal-memory | D. Bachtold et al., *Exp Brain Res* 136:128 (2001) |
| Thalamic pain syndrome | V. Ramachandran et al. *Neurocase*, iFirst, 1-4 (2007) |
| Vertigo | U.S. Pat. No. 6,748,275; U.S. Patent Application No. 2003/0195588 |

CVS activates various areas of the brain that are associated with specific disorders and/or symptoms. Table 2 highlights several such areas of the brain and provides an exemplary listing of some of the disease states/symptoms associated with each area. Without wishing to be bound by any particular theory, it is believed that thermal stimulation of the vestibular system is translated into electrical stimulation within the central nervous system ("CNS") and propagated throughout the brain, including but not limited to the brain stem, resulting in certain physiological changes that may be useful in treating various disease states (increased blood flow, generation of neurotransmitters, etc). See, e.g., Zhang, et al. *Chinese Medical J.* 121:12:1120 (2008) (demonstrating increased ascorbic acid concentration in response to cold water CVS). CVS can thus be used to induce serotonin output, ascorbic acid output, acetylcholine release, histamine release, vasopressin release, and/or the production of heat shock proteins with therapeutic value.

TABLE 2

Brain areas activated by CVS and disorders/symptoms associated with each area

| Brain Area Activated by CVS | Associated Disorders/Symptoms |
| --- | --- |
| Brain stem | hiccups, cranial nerve disorders, dizziness, facial weakness, nystagmus, voice alterations, vertical gaze problems, blurred vision, dysarthria, repiratory problems |

TABLE 2-continued

Brain areas activated by CVS and disorders/symptoms associated with each area

| Brain Area Activated by CVS | Associated Disorders/Symptoms |
| --- | --- |
| Cerbellum | vertigo, nystagmus, tremor, slurred speech, movement disorders |
| Cuneus/Precuneus | faulty visual processing |
| Fusiform gyrus | autism, faulty word/number recognition, faulty processing of color information |
| Hippocampus | Alzheimer's disease, memory dysfunction |
| Insula cortex | addiction, Alzheimer's disease, Parkinson's disease, neurodegenerative disorders, psychiatric disorders |
| Lingual gyrus | faulty visual processing |
| Parahippocampus | faulty memory encoding/retrieval |
| Parietal lobe | hemianesthesia, seizures, visual dysfunction, facial numbness, agraphia, dysgraphia, alien limb syndrome, spatial neglect |
| Putamen | extrapyramidal signs |
| Singular gyrus | schizophrenia, ADHD, OCD, mutism, mood disorders |
| Supplementary motor cortex | seizures, muscle weakness, spasticity |
| Temporal lobe | epilepsy, anomia, aphasia, dysphasia, parosmia, anger control |
| Thalamus | neuropathic pain, numbness |

Methods and devices used to provide CVS may also be used to stimulate cranial nerves within the ear. Activation and/or inhibition of these nerves may be used to treat a wide variety of disorders/symptoms. For example, stimulation of the vagus nerve and/or the trigeminal nerve is often used to moderate pain; and stimulation of the glossopharyngeal, trigeminal, and/or vagal nerves is associated with seizure suppression.

Importantly, pharmacological, electrical and/or electromagnetic nerve stimulation may provide synergistic benefits when combined with thermal stimulation resulting in CVS. The synergistic benefits of combining CVS with electrical or electromagnetic nerve stimulation may be especially prominent when the tissue(s) surrounding the nerve are cooled prior to warming the nerve. Such synergy occurs as a result of the temporal relationship between CVS and cranial nerve activation. Stimulating either the vestibular system or one or more of the cranial nerves leads to cortical activation which does not immediately diminish when the stimulus is removed. If a second stimulus is provided before the previous cortical activation has dissipated, the cortical activation arising from the second stimulus will be enhanced in those areas of the brain that respond to both CVS and cranial nerve stimulation.

For example, if a TED is first used to cool the ear canal and stimulate the subject's vestibular system, a certain level of cortical activation will be achieved (V). If the TED is then used to warm the ear canal and stimulate at least one cranial nerve, a certain level of cortical activation will be achieved (N). If the two stimuli occur close enough in time, the cortical activation resulting from the second stimulus will be enhanced by that fraction of V which has yet to dissipate when the second stimulus occurs ($V_2$), resulting in total cortical activation equal to at least $N+V_2$.

Accordingly, apparatuses and associated methods useful for delivering stimulation to the nervous system and/or the vestibular system of an individual are potentially beneficial to take full advantage of physiological responses that are useful in diagnosing and/or treating a variety of medical conditions.

SUMMARY OF THE INVENTION

A first aspect of the present invention is a tissue stimulator or probe configured for contacting to or insertion in the body of a subject to stimulate a tissue therein. The stimulator or probe comprises (i) a support configured for contacting to or positioning adjacent a tissue of the subject, and (ii) at least one thermoelectric device (TED) on the support and positioned for thermally (and/or electrically) stimulating the tissue.

A TED may be activated in various ways in accordance with the present invention, including but not limited to continuous activation, intermittent activation and cyclic activation. Such cyclic activation (e.g., heat then off and repeat, cool then off and repeat, heat then cool then off and repeat, cool then off then heat and repeat, etc.) may result in different types of waveforms, such as, for example, uniform, randomized, stochastic, etc., with each cycle lasting from about one minute to about ten minutes in duration. In some embodiments, the TED is configured to provide thermal pulses.

The foregoing and other objects and aspects of the present invention are explained in greater detail in the drawings herein and the specification set forth below. All United States patent references cited herein are specifically intended to be incorporated herein by reference in their entirety.

DETAILED DESCRIPTION

Figure 1:
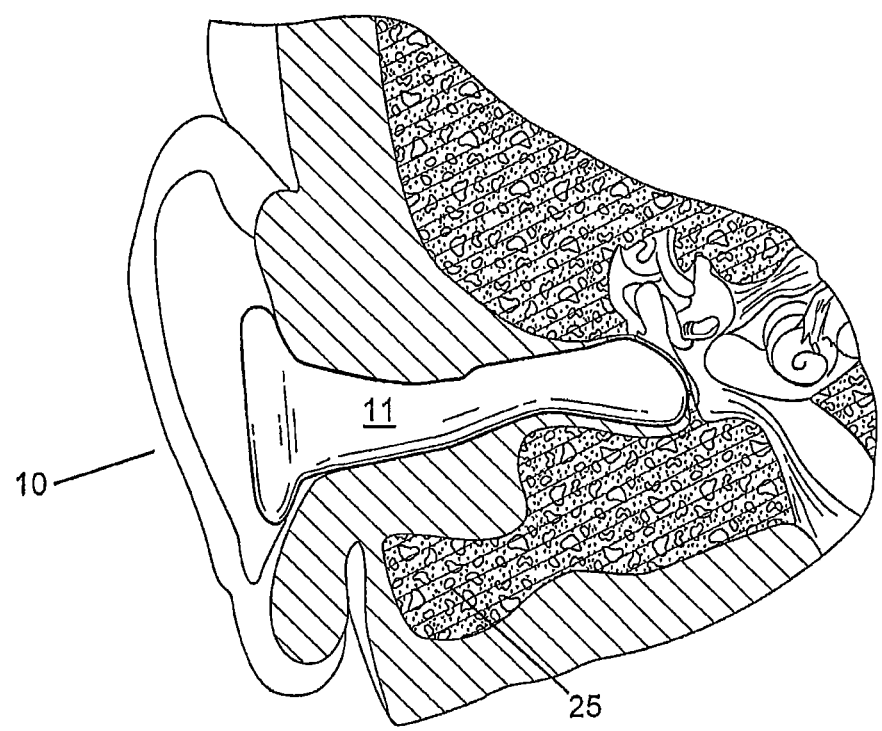
FIG. 1 illustrates a device of the present invention inserted in the ear canal of a human subject.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

As used herein, the term "and/or" includes any and all combinations of one or more of the associated listed items.

As used herein, the term "vestibular system" has the meaning ascribed to it in the medical arts and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

"Treatment," "treat," and "treating" refer to reversing, alleviating, delaying the onset of, inhibiting the progress of or preventing a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve.

The methods and systems of the present invention utilize TEDs to induce physiological and/or psychological responses in a subject for medically diagnostic and/or therapeutic purposes. Subjects to be treated and/or stimulated with the methods, devices and systems of the present invention include both human subjects and animal subjects. In particular, embodiments of the present invention may be used to diagnose and/or treat mammalian subjects such as cats, dogs, monkeys, etc. for medical research or veterinary purposes.

As noted above, the present invention provides a tissue stimulator or probe (e.g., a nerve stimulator and/or a caloric vestibular stimulation apparatus) configured for contacting to or insertion in the body of a subject (particularly, but not limited to, a human subject) to stimulate a tissue therein. The stimulator or probe comprises: (i) a support configured for contacting to or positioning adjacent a tissue of the subject; (ii) at least one TED (e.g., a thin film thermoelectric transducer) on the support and positioned for thermally stimulating the tissue.

In some embodiments, the at least one thermoelectric device comprises a plurality of thermoelectric devices (e.g., at least 3, 5 or 10, up to 20, 50 or 100 or more), each of the plurality of thermoelectric devices positioned on the support for stimulating the tissue (with each of the plurality of TEDs being optionally, but in some embodiments preferably, separately activatable or addressable from one another).

In some embodiments, the plurality of TEDs are positioned adjacent one another on the support at a density of from 5, 10 or 20 per square centimeter (e.g., up to 100, 200 or 400 per square centimeter, or more).

In some embodiments, the plurality of TEDs are positioned adjacent one another in a linear array; in other embodiments, the plurality of TEDs are positioned adjacent one another in a two-dimensional array.

In some embodiments, the plurality of TEDs are thermally coupled to one another.

In some embodiments, each of the TEDs has a first side and a second side, the first side thermally coupled to a heat transfer structure and the second side positioned for thermally stimulating the tissue so that the TED is thermally coupled between the heat transfer structure and the tissue.

In some embodiments, the plurality of adjacent TEDs are thermally coupled to one another (e.g., through a common heat transfer structure), so that thermal energy displaced by one thereof can be at least partially offset by thermal energy displaced by an adjacent one thereof (e.g., by heating tissue with one device while cooling adjacent tissue with another device).

In some embodiments, the stimulator is a probe having a distal end portion and an elongate body portion (the probe may optionally be a catheter having an elongate lumen formed therein in fluid communication with an opening formed at the distal end portion).

In some embodiments, at least one, or a plurality, of the TEDs is located at the probe or catheter distal end portion, and wherein the elongate body portion is optionally insulated. In other embodiments, a plurality of TEDs are positioned along the elongate body portion. Optionally, in some embodiments, the elongate body portion has at least two elongate side face portions, and wherein a plurality of the TEDs are positioned along each of the at least two elongate side face portions.

In some embodiments, the tissue stimulator further comprises at least one electrode (or a plurality of electrodes) on the probe for electrically stimulating the tissue.

The tissue stimulator may further comprise a plurality of thermal stimulation conductive lines, each of the plurality of TEDs electrically coupled to at least one separate thermal stimulation conductive line.

In some embodiments, the stimulator may further comprise a plurality of electrical stimulation conductive lines, each of the plurality of TEDs electrically coupled to at least one separate thermal stimulation conductive line.

In some embodiments, the plurality of separate conductive lines are bundled together in a single lead, the lead having a terminal connector configured for connection to a controller.

In some embodiments of the foregoing (adapted for caloric vestibular stimulation and/or stimulation of one or more cranial nerves), the support is configured as an ear insert so dimensioned as to be insertable into the ear canal of a wearer.

A further aspect of the invention is a system comprising: (i) a tissue stimulator as described above, and (ii) a controller electrically coupled to the TED, wherein the controller is configured to sense a first value of an electrical characteristic of the TED, to generate a first electrical control signal to pump heat through the TED in response to sensing the first value of the electrical characteristic of the TED, to sense a second value of the electrical characteristic of the TED wherein the first and second values of the electrical characteristic are different, and to generate a second electrical control signal to pump heat through the TED in response to sensing the second electrical characteristic of the TED, wherein the first and second electrical control signals are different.

In some embodiments, the controller is configured to sense the first and second electrical characteristics by sensing electrical signals generated by the TED responsive to first and second heat gradients across the TED.

In some embodiments, the controller is configured to generate the first electrical control signal so that heat is pumped through the TED in a first direction, and to generate the second electrical control signal so that heat is pumped through the TED in a second direction opposite the first direction.

In some embodiments, the controller is configured to generate the first electrical control signal so that a first electrical current flows through the TED in a first direction, and to generate the second electrical control signal so that a second electrical current flows through the TED in a second direction opposite the first direction.

In some embodiments, the TED comprises a thermoelectric material such as bismuth telluride.

In some embodiments, the TED comprises a P-type thermoelectric element and an N-type thermoelectric element electrically coupled in series and thermally coupled in parallel.

In some embodiments, the system further comprises a heat transfer structure thermally coupled to a first side of the TED; and a temperature controlled medium thermally coupled to a second side of the TED so that the TED is thermally coupled between the heat transfer structure and the temperature controlled medium. In some embodiments thereof, the controller is configured to generate the first and second electrical control signals to maintain a stable temperature of the temperature controlled medium. In some embodiments thereof, the controller is configured to generate the first and second electrical control signals to provide a temperature ramp for the temperature controlled medium. In some embodiments thereof, the controller is configured to generate the first and second electrical control signals to provide a cyclical temperature profile for the temperature controlled medium.

The present invention can, in some embodiments, be implemented with the temperature control systems and/or other methods and apparatuses described in U.S. patent application Ser. Nos. 12/669,684, 12/693,016, 12/166,953, and 11/972,267; U.S. Provisional Application No. 61/224,668; and PCT Application No. PCT/US2008/071935.

Thermoelectric Devices

Any suitable TED or transducer can be used to carry out the present invention, including, but not limited to, those described in U.S. Pat. Nos. 7,205,675; 7,098,393; 7,024,865; and 5,974,806; and in United States Patent Publication No. 2004/0199266. See also Riffat and Ma, *Applied Thermal Engineering* 23:913 (2003). The transducer can be an electrothermal textile transducer, including, but not limited to, those described in U.S. Pat. Nos. 7,202,443; 6,977,360; and 6,229,123. The transducer is typically provided with a lead which may be connected to an external power supply and controller, or the power supply and controller may be contained within the device as discussed further below. The devices disclosed herein further include embodiments of thermoelectric transducers in all shapes and sizes, including but not limited to spiral and helical shapes.

In some embodiments, a plurality of TEDs may be mounted on an elongated flexible strip by any suitable technique, including, but not limited to, those described in Hiller et al., U.S. Pat. No. 7,147,739. In other embodiments, where it is desired to generate an electric current from the transducer, the transducer can be a mechanical or piezoelectric transducer. Examples include, but are not limited to, both piezoelectric devices and zinc-oxide nanowire nanogenerators. See, e.g., Wang, *Science* 316:102 (Apr. 6, 2007). Wang, *Science* 312:242 (Apr. 14, 2006); Patel-Predd, *MIT Tech. Rev.* (Apr. 5, 2007).

Thin film TEDs or transducers are preferred as transducers in some embodiments, including, but not limited to, the thin film TEDs described in U.S. Pat. No. 6,300,150 and United States Patent Publication Nos. 2007/0028956 and 2006/0086118. Such thin film TEDs may also advantageously incorporate a temperature sensing function, so that temperature sensing can be accomplished through the same device without the need for a separate temperature sensor.

In some embodiments, the TED comprises a thermoelectric material such as bismuth telluride.

In some embodiments, the TED comprises a P-type thermoelectric element and an N-type thermoelectric element electrically coupled in series and thermally coupled in parallel.

Ear Inserts for CVS and/or for Cranial Nerve Stimulation

Figure 2:
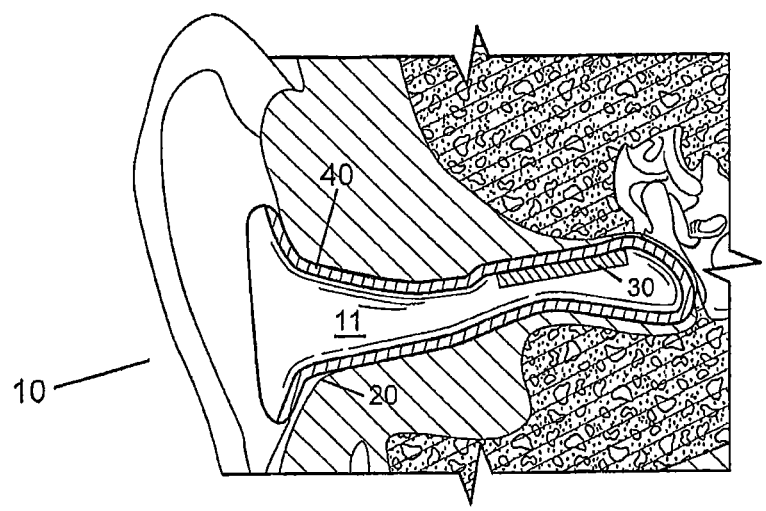
FIG. 2 is a further side-section illustration of the device of FIG. 1.

FIGS. 1 and 2 illustrate a first embodiment of a device 10 of the present invention inserted in the ear of a human subject (the anatomical portion of the figures is adapted from FIG. 2 of U.S. Pat. No. 4,244,377). The device 10 comprises an ear insert 11 so dimensioned as to be insertable into the ear canal 20 of a subject. The ear insert has an inner portion 12, with the inner portion preferably having a length dimension at least as great as a major portion of the length dimension of the ear canal of the subject (e.g., a length at least 50, 60, 70, or 80 percent that of the length dimension of the ear canal of the subject).

As shown in FIG. 2, the ear insert 11 further includes at least one thermoelectric transducer 30 attached to the insert 11 for providing CVS and/or cranial nerve stimulation to the individual. The thermoelectric transducer 30 may be contained entirely within the insert 11 or may be attached to an optional, separate sleeve 40 described above. The thermoelectric transducer 30 used in the device 10 may be a thermoelectric cooler common in the industry today. The thermoelectric transducer 30 is capable of providing caloric stimulation to the individual's outer and/or inner ear by allowing for the transfer of heat to and from the ear canal 20, thereby raising and lowering the temperature within the ear canal 20 as desired. The ear canal serves as a useful conduit to the individual's vestibular system and to the cranial nerves described above.

The ear insert 11 can be formed of any suitable material, including flexible materials (particularly where the ear insert is shaped in conformance with the ear canal of the subject) and rigid materials (e.g., when a more cushioning sleeve may be utilized). The ear insert 11 can be formed by any suitable technique, such as molding or casting, with the TED 30 or transducer (and any associated wires or leads) cast or molded in place in accordance with conventional techniques.

The ear insert 11 can, in some embodiments, have one or more canals formed therein to facilitate or permit natural ventilation of the ear, as described in U.S. Pat. No. 6,819,770. If desired for some embodiments, the ear insert 11 can also include an acoustic transducer for delivering auditory or sound stimuli to the subject.

As shown in FIG. 2, a sleeve or sheath 40 may cover and/or may be connected to (e.g., removably connected to; permanently connected to; or formed on) the ear insert inner portion 12. As shown most clearly in FIG. 4, the optional sleeve may have a closed medial end portion 41 and an open outer end portion 42. In some embodiments, the sleeve 40 has an inner surface portion configured 45 to conformably engage the ear insert inner portion 12, and an outer surface portion 46 configured to conformably engage the ear canal 20 of the subject. Hence, heat can be conducted between (that is, to or from) each of the at least one thermoelectric transducers 30 and the ear canal 20 through the sleeve 40 to deliver CVS and/or cranial nerve stimulation to the subject.

In some embodiments, the optional sleeve may comprise areas of high thermal conductivity (high-k) and areas of low thermal conductivity (low-k) such that different portions of the ear canal receive different levels of, or no, thermal stimulus (i.e., portions of the ear canal that are adjacent to a low-k area of the sleeve receive a weaker thermal stimulus than portions of the ear canal that are adjacent to a high-k area of the sleeve). In some embodiments, the optional sleeve may comprise only high-k areas or only low-k areas.

In embodiments lacking the optional sleeve, the ear insert inner portion 12 may similarly comprise high-k and low-k areas whereby portions of the ear canal may be stimulating differentially or not at all.

Figure 3:
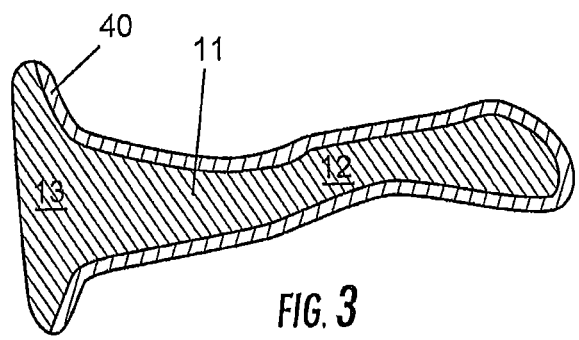
FIG. 3 is a side-section illustration of one embodiment of the invention, in which the ear insert inner portion has a shape that corresponds to the ear canal of the subject.
Figure 4:
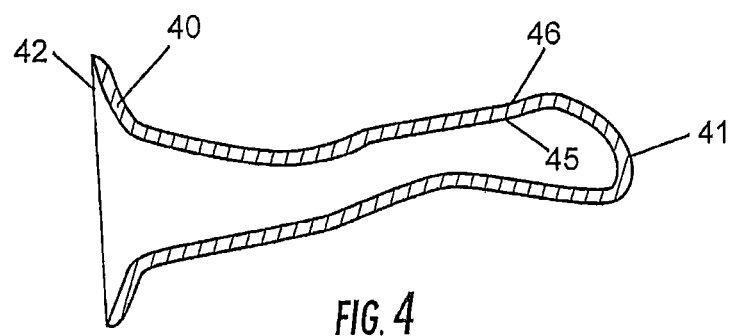
FIG. 4 is a side-section illustration of the optional sleeve of the device of FIG. 3 removed from the ear insert.
Figure 5:
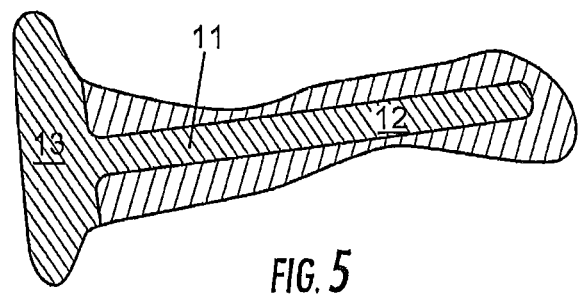
FIG. 5 is a side-section illustration of another embodiment of the invention, in which the optional sleeve outer portion has a shape that corresponds to the ear canal of the subject.
Figure 6:
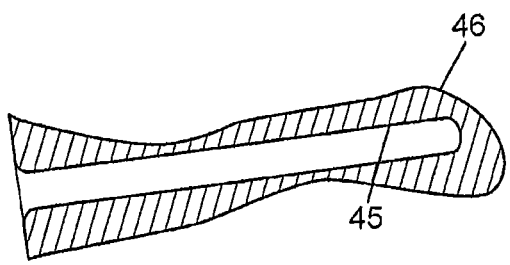
FIG. 6 is a side-section illustration of the optional sleeve of the device of FIG. 5 removed from the ear insert.

In some embodiments, such as shown in FIGS. 3-4, the ear insert inner portion 12 has a shape (i.e., a preformed shape) that corresponds to the ear canal 20 of the subject. In such an embodiment the optional sleeve 40 may be configured to correspond to the shape of the ear insert inner portion 12, but conforms to the ear canal 20 of the subject only when mounted on the optional sleeve insert inner portion 12. In other embodiments, such as shown in FIGS. 5-6, the ear insert inner portion 12 does not have a shape that corresponds to the shape of the ear canal 20 of the subject, but the optional sleeve outer surface portion 46 instead has a shape (i.e., a preformed shape), that corresponds to the ear canal of the subject. Both embodiments provide, when assembled, a sleeve inner surface portion 45 that conformably engages the ear insert inner portion 12, and an outer surface portion 46 that conformably engages the ear canal 20 of the subject. Hence, in both embodiments heat can be conducted between each of the at least one thermoelectric transducers 30 and the ear canal 20 through the optional sleeve 40, as discussed above.

The optional sleeve 40 can comprise, consist of, or consist essentially of any suitable elastic and/or compressible material, such as a polymer, a textile (woven or non-woven) or a composite thereof. In some embodiments the polymer comprises a hydrogel polymer, a thermally conductive resin, and/or a viscoelastic polymer (it being understood that some but not all viscoelastic polymers will be hydrogel polymers; and some but not all hydrogel polymers will be viscoelastic polymers). Numerous suitable hydrogel polymers, including biodegradable or bioerodable hydrogel polymers, and stable hydrogel polymers (e.g., silicone hydrogel polymers) are known. Examples include but are not limited to those described in U.S. Pat. Nos. 7,213,918; 7,171,276; 7,105,588; 7,070,809; 7,060,051; and 6,960,625. Suitable viscoelastic polymers include but are not limited to those described in, for example, U.S. Pat. Nos. 7,217,203; 7,208,531; and 7,191,483. An ester-based viscoelastic memory foam such as used in the heating pad systems described in U.S. Pat. No. 7,176,419 is among those suitable for use in making sleeves of the present invention. In some embodiments, the optional sleeve 40 has a thermal conductivity of from 0.1 to 50 W/m×K; and a hardness of from 0 to 50 on the Shore A scale.

The optional sleeve 40 can be made by any suitable technique such as molding, casting, etc. While in some preferred embodiments the optional sleeve 40 is removable, in other embodiments that sleeve is formed on, integrally formed with, or otherwise permanently connected to the ear insert 11. The optional sleeve 40 can be open at both the medial 41 (closest to the ear drum) and outer ends 42 thereof, or open at the outer end 42 only. When the ear insert 11 has one or more canals formed therein to facilitate ventilation of the ear, the optional sleeve 40 is preferably open at both the proximal and distal ends of the canal. The optional sleeve 40 may be transparent or tinted with a pigment, in whole or in part such as in one or more defined locations on the sleeve (e.g., the medial portion, the outer portion, the upper portion, the lower portion, the front portion, the back portion) to provide an indicator of whether the sleeve is for a left or right ear canal device, an indicator of size of the sleeve, an indicator of how the sleeve should be oriented on the insert, etc.

Devices of the present invention can be used singly or in pairs. The ear insert 11 can optionally include an identifier associated therewith for indicating whether said ear insert is configured for insertion into a left or right ear canal. Likewise, the optional sleeve 40 can optionally include an identifier associated therewith for indicating whether said sleeve 40 is configured for: (i) insertion into a left or right ear canal, or (ii) engagement on said ear insert inner portion when said ear insert is configured for insertion into a left or right ear canal. Such identifiers can be printed, stamped, or molded symbols such as "L" for left and "R" for right; color coding for left and right; etc.

In FIGS. 1, 2, 3 and 5 the ear insert 11 has an outer portion 13, the outer portion 13 configured to overlie at least a portion (e.g., some or all) of the external ear 22 of a subject. This creates an external appearance, when worn, similar to that of a half-shell or full-shell hearing aid. However, any suitable configuration can be utilized, as further shown in FIGS. 9-10, in which the device is configured to be positioned in the canal or completely in the canal of the subject. Note also in FIG. 10 that the device medial portion 14 does not abut the eardrum, as would the medial portion 14 of the device of FIG. 9.

Figure 7:
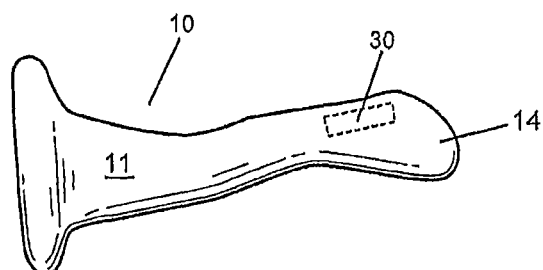
FIGS. 7-10 illustrate various alternate embodiments of the invention, of different length dimension, and with different transducer arrangements.
Figure 8:
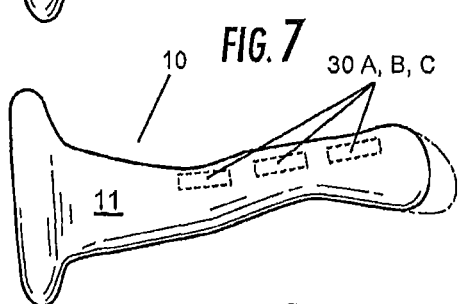
Figure 9:
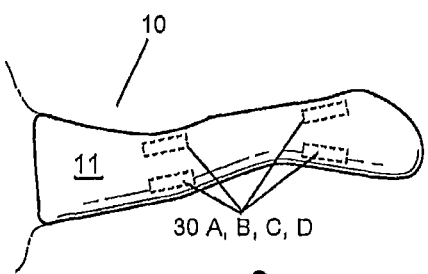
Figure 10:
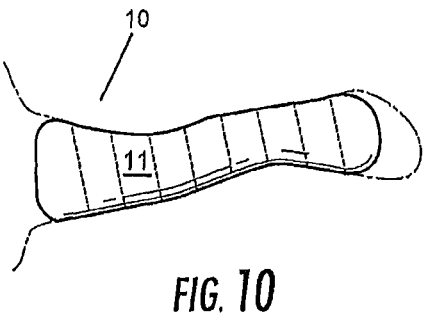
Figure 11:
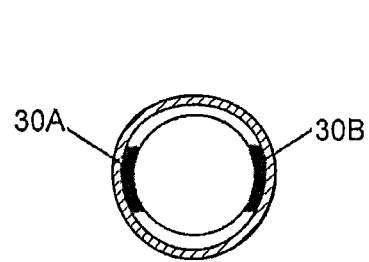
FIGS. 11-12 are cross-sectional illustrations of embodiments of the present invention, showing different transducer arrangements.
Figure 12:
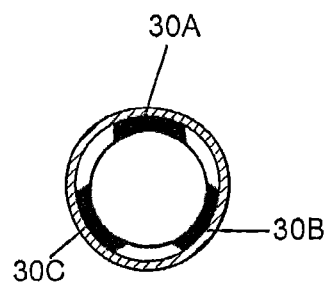

FIGS. 7-12 illustrate various transducer arrangements in devices of the present invention. While a single thermoelectric transducer 30 can be used, in some embodiments it is preferable to include at least two, three, or four (or more) separately controllable thermoelectric transducers 30a, 30b, 30c, 30d, which can be spaced apart from one another on the ear insert inner portion 12. As shown in FIGS. 7-9, the transducers can be positioned longitudinally along the insert 11; as shown in FIG. 10, the transducers 30 can be positioned laterally along the insert 11. Other positionings, such as angled positionings, and combinations of the foregoing, can also be used. Further, while the transducers are depicted as rectangular in shape, any suitable regular or irregular shape can be used.

Figure 13:
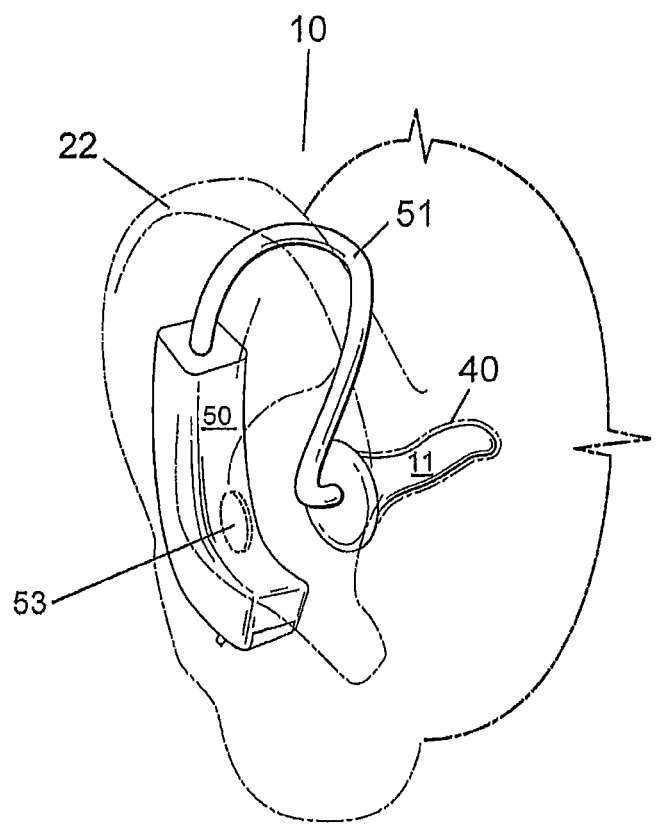
FIG. 13 illustrates an embodiment of the present invention that includes an external body portion configured for positioning behind the ear of a subject.
Figure 14:
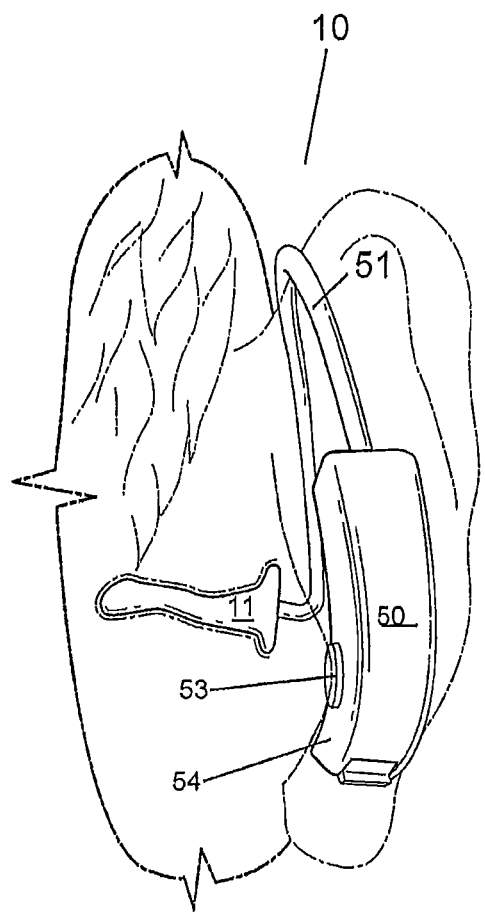
FIG. 14 is a further illustration of the embodiment of FIG. 13 from behind the subject, showing the additional external transducer positioned on or adjacent the mastoid process of the subject.

FIGS. 13-14 illustrate a further embodiment of the present invention, in which an external housing 50 is connected to the ear insert by a bridge member 51 (here, in the shape of a tube). The external housing 50 is configured for positioning behind the ear of a subject. The housing 50 can contain a computerized control module, control circuitry, a power supply such as a battery, controls such as an on-off switch, etc. In the illustrated embodiment the housing has an external transducer 53 mounted on the medial surface 54 thereof, which external transducer can deliver thermal, electric, or mechanical stimuli to the subject at sub-threshold (e.g. stochastic) or super-threshold levels, which stimuli may be given in any suitable pattern alone or in cooperation with stimuli from the ear canal transducers. Note that the external transducer can be positioned on the housing so that it contacts the subject on or adjacent to the mastoid process 25 of the subject.

The bridge member 51 may be thermally coupled to the thermoelectric transducer(s) and serves as a heat sink, removing excess heat from the transducers and assisting in the transfer of excess heat to the atmosphere. The external housing 50 may likewise serve as a heat sink. The presence of such a heat sink may help to optimize the waveform characteristics of the thermal stimulus by facilitating heat dissipation, thus optimizing the rate of waveform pattern change.

Figure 15:
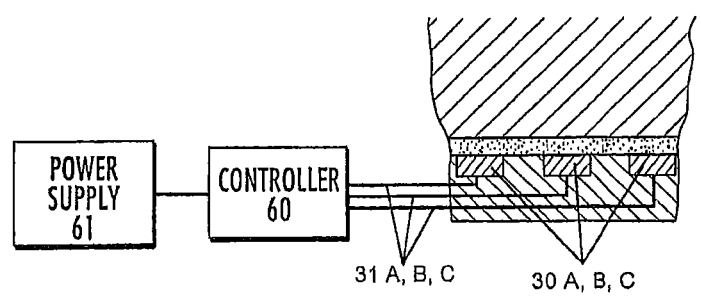
FIG. 15 is a schematic illustration of an apparatus of the invention operatively associated with a power supply and controller.

FIG. 15 schematically illustrates a device of the present invention operatively associated with a controller 60, which controller is in turn operatively associated with a power supply. The controller and power supply can be contained within the device (e.g., in an external housing as described in connection with FIGS. 13-14 above), in a belt-worn or other housing, connected to a stationary unit such as a personal computer, or in any other suitable configuration. In a preferred embodiment, the controller includes a computerized control module programmed with computer instructions (i.e., software) that controls the magnitude, duration, wave pattern, and other attributes of the vestibular stimulation.

As shown in FIG. 15, once the device is positioned within the ear canal 20 of a subject, the at least one thermoelectric transducer 30a, 30b, 30c, each of which is operatively associated with the controller by a separate lead 31a, 31b, 31c, is activated for a time and to a temperature sufficient to deliver CVS and/or cranial nerve stimulation to the subject. An adjustable or programmable control module can be utilized to optimize stimulation for a particular subject, and for a particular purpose or condition. Where (as shown in FIG. 15) there are at least two separately controllable thermoelectric transducers on the ear insert inner portion spaced apart from one another, the activating step can comprise separately and selectively activating the at least two separately controllable thermoelectric transducers (e.g., by activating only one or two thereof, by heating one transducer and cooling another; by sequentially activating transducers; by activating different transducers to different degrees; combinations of some or all of the foregoing, etc.) Patterns of separate and selective activation can be preprogrammed, can be determined empirically, can be optimized by the subject or a programmer (such as a clinician) in a programming session with the subject, etc.

The control module can be part of a multimodal stimulation system for creating a "virtual environment" for the subject, such as described in U.S. Pat. No. 5,762,612 to Campbell. If desired, the device can incorporate sensors or monitoring probes for positioning in the ear canal, such as described in United States Patent Publication Nos. 2007/0112277 and 2005/0209516.

Subjects for the devices of the present invention are often, but are not limited to, human subjects, including both male and female subjects at any stage of development (e.g., juvenile, adolescent, adult, and geriatric subjects). While the shape of ears and ear canals 20 will vary among subjects, and different sizes and combinations of ear inserts and optional sleeves will likely be necessary to accommodate different subjects, an optimal set of inserts and optional sleeves can be developed through the use of statistical shape analysis (see, e.g., Paulsen, Statistical Shape Analysis of the Human Ear Canal with Application to In-the-Ear Hearing Aid Design (Kongens Lyngby 2004)) to provide ready availability of the devices of the present invention without the need to custom-mold a device for each individual subject, including, but not limited to, through the added adaptability between subjects contributed by the compressible optional sleeve 40 portion.

In some embodiments, an insert 11 of the invention is preformed to conform to, and hence conformably engage, the ear canal 20 of a particular subject. Such a preformed insert 11 can be produced by forming an ear impression, which ear impression can then be used for casting in analogous manner as described in U.S. Pat. No. 6,249,587, or can instead be scanned and utilized for subsequent casting, three-dimensional ink-jet printing, and/or other three dimensional construction (via deposition or removal of materials), as described in U.S. Pat. Nos. 7,162,323; and 6,986,739 (see also Fuller, *J. Microelectromechanical Systems* 11:54 (2002). With such a preformed device any possible need for a sleeve may be obviated, although it is preferred, but not required, that the ear insert itself comprise or be formed of a soft resilient material (e.g., having a hardness of from 0 to 50 on the Shore A scale).

Figure 16:
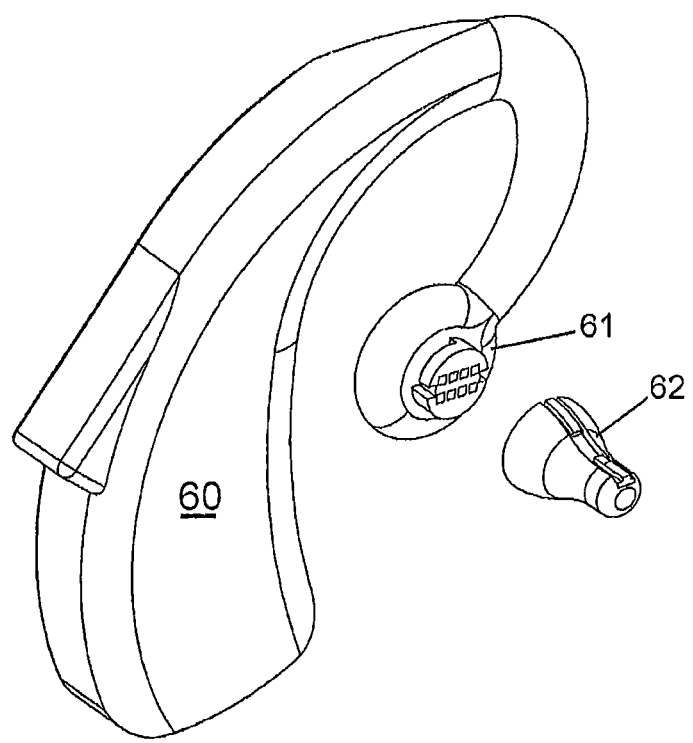
FIG. 16 is a schematic illustration of an apparatus in which the components therein are modular.
Figure 17:
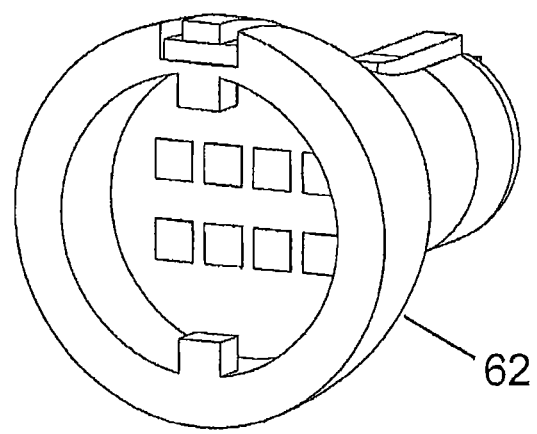
FIG. 17 is a schematic illustration of that portion of a modular insert engaging the ear canal.

A different embodiment of the vestibular and/or cranial nerve stimulating device 10 is shown in FIGS. 16 and 17. In this embodiment, which is in no way limiting of the invention, the device includes the ear insert, thermoelectric transducer, electrode, and computerized control module described above. As shown in FIGS. 16 and 17, however, the active elements on the insert 62, including any transducer or electrode, occupy adjustable positions for greater control over the device 10. The ability to adjust the position of the active elements on the insert allows for greater flexibility in directing stimulation in a way that is customized for that person. Minor changes in the direction and location of output can have large consequences for different individuals. As shown in FIGS. 16 and 17, one embodiment of the device includes modular portions 60, 61, 62 that fit together and come apart for greater variety in positioning the output. The modular structure shown in FIGS. 16 and 17 also allows for interchangeable ear inserts to be used with a single control module housed in the outer portion of the device.

Interchangeable ear inserts 62 are useful to allow for a variety of modifications in keeping with the scope of this invention. For example, a single individual might require diagnosis or therapy with fewer or greater numbers of any active element. As noted herein, the device 10 includes the flexibility to increase or reduce the number of electrodes, transducers, or other active elements necessary to achieve a desired result. Also, the modular nature of the device shown in FIGS. 16 and 17 allows for portions or pieces of the device 10 to be replaced without replacing the whole device. An ear insert 62 might be less expensive to replace than the computerized control module. Accordingly, FIGS. 16 and 17 illustrate schematically one embodiment of a modular vestibular stimulation device in which the active elements, located on either the ear insert 62, or possibly a sleeve 40 as described above, are attached to an outer portion 61 via standard electrical connectors.

Figure 18:
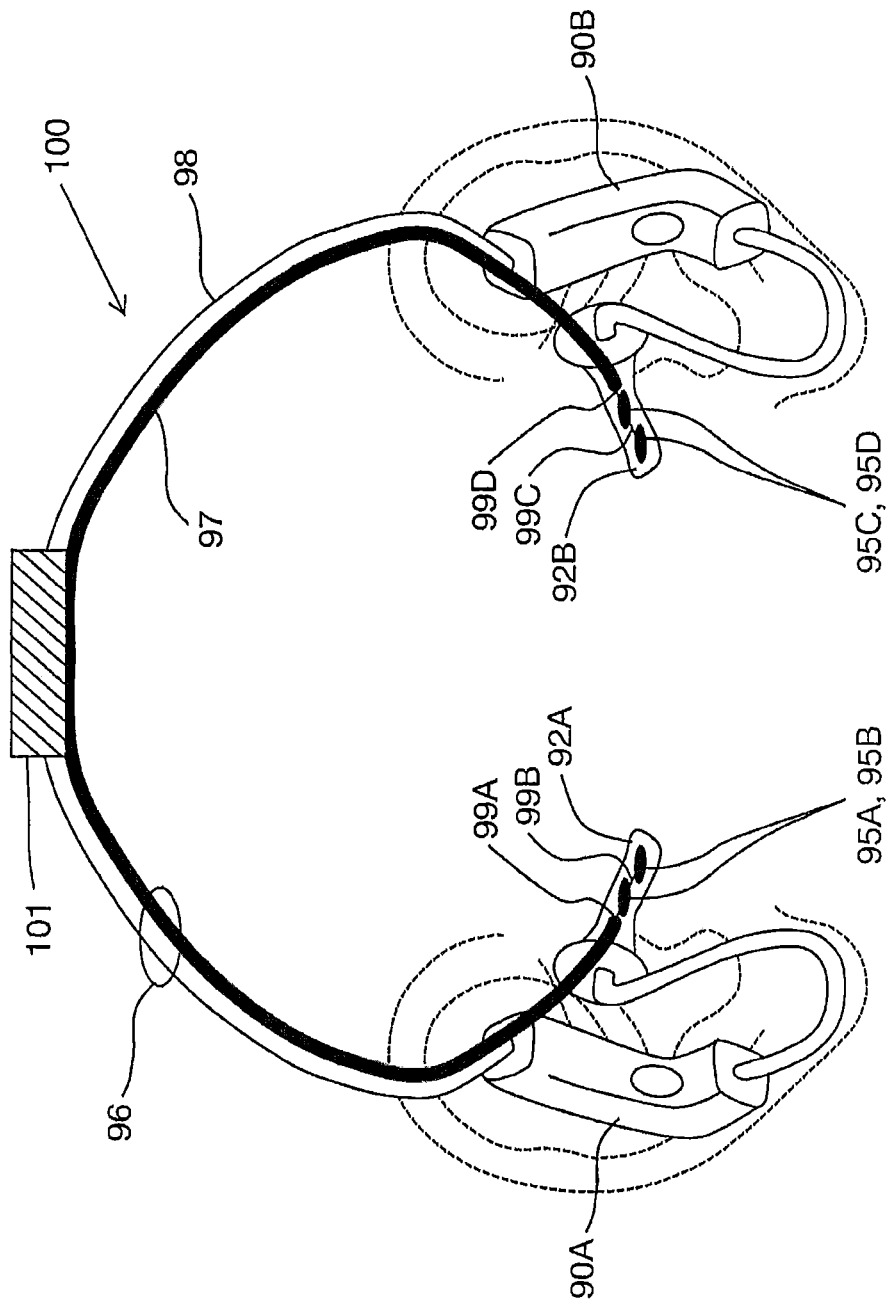
FIG. 18 illustrates two devices of the present invention incorporated into a single device that can be worn as a headset assembly.

The devices disclosed herein can be used in pairs. Accordingly, FIG. 18 shows an embodiment of the present invention that allows significant control over treatment options in either ear or both ears. Such a configuration is useful to complete particular assessments, diagnoses or therapies on different sides of a patient's brain. The embodiment of FIG. 18 takes the individual stimulation devices, i.e., the ear inserts 92A, 92B, and incorporates them into a single device that can be worn as a head set assembly 100.

The head set assembly 100 includes a head band 96 serving as a headset body portion that assists the subject in achieving a proper fit for inserts 92A, 92B positioned into the ear canal. By making the head band 96 of a pliable material, the subject can adjust the depth to which the inserts 92A, 92B engage the ear canal and stay in place.

FIG. 18 also shows a modification to previously described embodiments by which the head set assembly 100 includes an extensive heat sink capacity in the form of head band heat sink portion 97 extending along one side of the head band 96. The heat sink portion 97 terminates on either end at thermoelectric transducers 95A, 95B, 95C, 95D installed on the ear inserts 92A, 92B. As the thermoelectric transducers remove heat from the inner ear or surrounding tissue, the heat sink portion 97 removes the excess heat from the transducers 95A, 95B, 95C, 95D via heat sink extensions 99A, 99B, 99C, 99D associated with each respective transducer 95A, 95B, 95C, 95D. The heat sink extensions 99A, 99B, 99C, 99D are independently connected to the head band heat sink portion 97, which has more than sufficient capacity to transfer heat from the transducers 95A, 95B, 95C, 95D to the atmosphere.

The head set assembly 100 also accommodates multiple variations of control systems used in accordance with this invention. As shown in FIG. 18, each insert 92A, 92B may optionally be connected to power and control circuitry in respective external housings 90A, 90B. The external housing 90A, 90B can contain a computerized control module, control circuitry, a power supply such as a battery, controls such as on-off switches, etc. The external housing 90A, 90B, therefore, may include all of the electronics necessary for programming and controlling a course of therapy on either side of the subject's head, all the while assisting in disposing of excess heat via the heat sink structures 97, 99.

Figure 19:
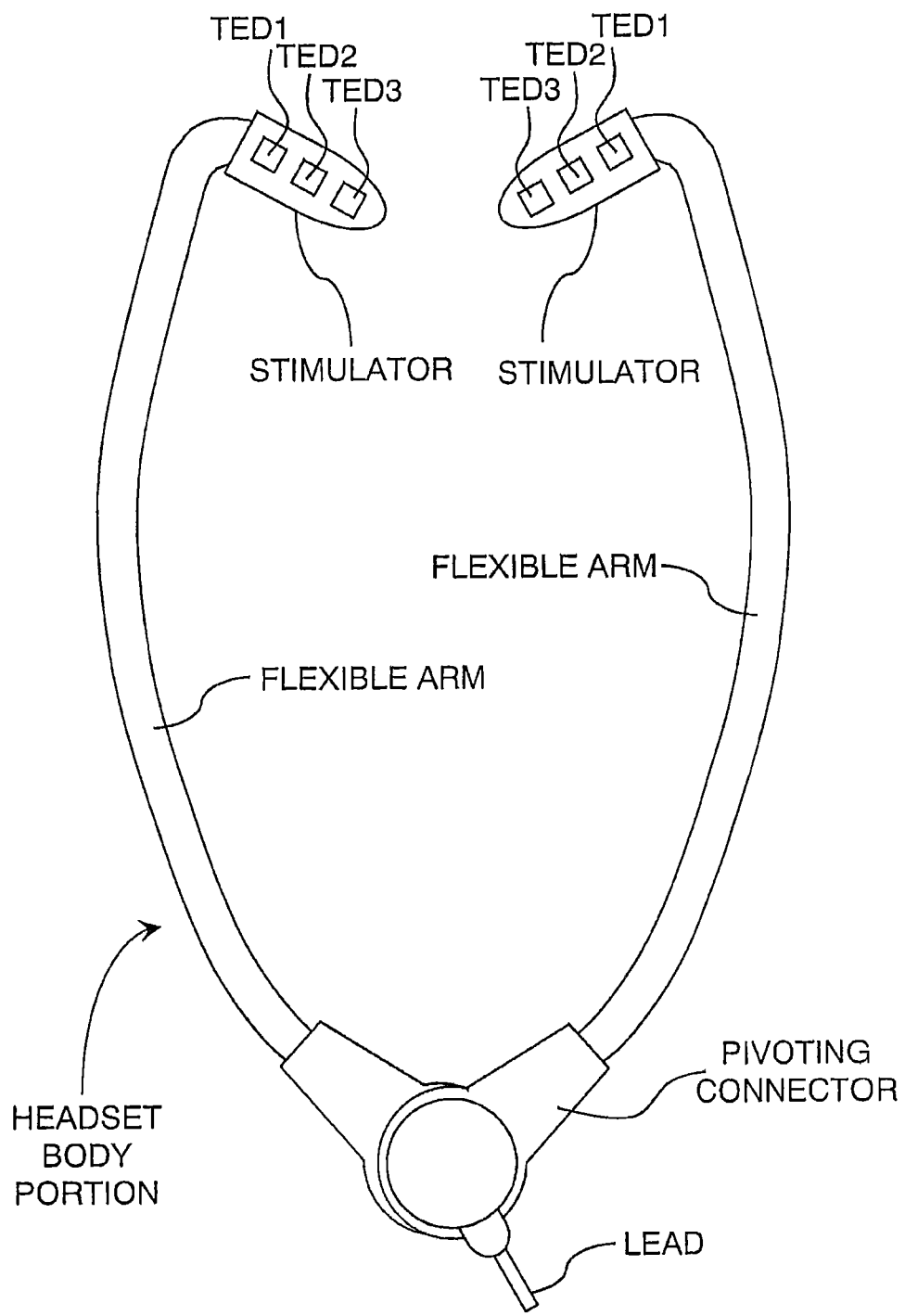
FIG. 19 illustrates two devices of the present invention incorporated into a single device that can be worn like a stethoscope.

In certain circumstances, the head set assembly 100 is most effective if both inserts 92A, 92B have the capacity for communicating with a common control system. FIG. 19 shows this control system included in universal control enclosure 101 located at the top of the head band 96. The head set assembly 100 incorporates a communications link 98 that extends across the head band to the external housings 90A, 90B to coordinate the stimulation given by respective thermoelectric transducers 95A, 95B, 95C, 95D. In other embodiments, the universal control enclosure 101 may include sufficient power circuitry and controllers to reduce or eliminate the need for the external housings 90A, 90B. For optimal utility and comfort, however, the subject may prefer certain components, such as batteries, to be worn in the external enclosures positioned behind the ear or elsewhere.

Overall, the embodiment of FIG. 18 allows multiple thermoelectric transducers 95A, 95B, 95C, 95D to be controlled via control circuitry to provide heating, cooling, and/or electrical stimulation to nerve endings in the ear as well as the vestibular system. The heat energy is regulated by the conveniently positioned heat sink portion 97 on the head band 96.

It will be appreciated that, while the head band is shown as being worn over the head, it could also be positioned behind the head (as shown in FIG. 7A of U.S. patent application Ser. No. 12/166,953), or under the head in an arrangement like a stethoscope as shown in FIG. 19.

It will also be appreciated that, while the head set assembly 100 is shown as comprising two ear inserts 92A, 92B, a head set assembly could also be configured with a single ear insert 92A or 92B.

In the embodiment illustrated in FIG. 19, each ear insert comprises a plurality of TEDs, where the TEDs are thermally coupled to one another (e.g., by sharing a common heat transfer structure or heat sink). Hence the need for an external heat sink as shown in FIG. 18 is reduced or obviated, at least when the device can be adjusted so that some of the TEDs are utilized to heat tissue (cool the heat transfer structure) while others are concurrently utilized to cool tissue (heat the heat transfer structure).

Figure 20:
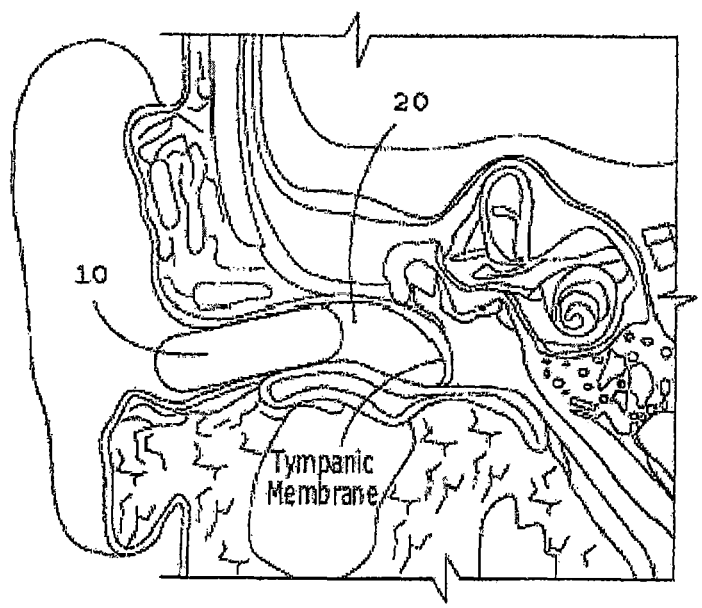
FIG. 20 illustrates a device of the present invention inserted in the ear canal of a human subject.

FIG. 20 illustrates yet another embodiment of the present invention. In such embodiments, the vestibular system and/or cranial nerve stimulation device 10 is so dimensioned as to be insertable into the ear canal 20 of a subject, but does not have a length dimension at least as great as a major portion of the length dimension of the ear canal of the subject (e.g., a length at least 50, 60, 70, or 80 percent that of the length dimension of the ear canal of the subject).

The vestibular system and/or cranial nerve stimulation device 10 may be operational as an individualized piece of equipment worn by a single user, similar to the way a person wears a hearing aid. In different embodiments, however, the device 10 can be incorporated into a larger medical system. In one embodiment, the computerized control module connects to peripheral equipment for added functionality. In a preferred embodiment, the device 10 is part of a larger therapeutic system that includes other devices for monitoring physiological parameters. Without limiting the types of peripheral equipment connecting to the device described herein, one useful peripheral sensor measures galvanic skin resistance. Skin resistance is a significant factor in estimating certain physiological and emotional changes that an individual is experiencing. When data tracking skin resistance are combined with data tracking a circadian cycle, such as the temperature cycle, the result is a broader, more holistic approach to treating an individual. Skin resistance also provides information regarding changes and phase shifts to the circadian cycle and is therefore useful as a feedback check on the effectiveness of any currently administered vestibular stimulation. Accordingly, in one aspect, the device 10, particularly the computerized control module, processes data gathered by peripheral devices, such as a galvanic skin resistance, and adjusts device 10 output accordingly. In line with this galvanic skin resistance model, the device is useful for practicing a method of delivering vestibular stimulation and/or cranial nerve stimulation to an individual's brain. In one embodiment, the method includes (i) arranging a thermal transducer 30 and an electrode on an ear insert 11 in a position to stimulate the vestibular system and/or at least one cranial nerve of the subject, (ii) electronically connecting the transducer 30 and the electrode to a controller, and (iii) supplying the controller with galvanic skin resistance data and temperature data from the individual. Next, the device 10 activates the transducer 30 and the electrode via the controller. The transducer regulates heat exchange within the ear canal for a time and to a temperature sufficient to deliver vestibular stimulation to the individual. Similarly, the electrode provides electrical stimulation to the vestibular system according to pre-set functions within the controller. In combination, the controller, the transducer 30, and the electrode deliver vestibular stimulation, wherein the vestibular stimulation is selected from caloric stimulation, electrical stimulation, and combinations of each. The method further includes the step of measuring physiological changes in the individual, wherein the physiological changes are selected from the group consisting of brain temperature changes, brain chemistry changes and blood chemistry changes. The step of measuring physiological changes can be selected from the group consisting of circadian temperature cycle time shifts, ascorbic acid production, serotonin production, histamine production, vasopressin production, acetylcholine production, and/or heat shock protein production. Brain temperature should probably be included since it reflects the metabolic state of activated/inactivated tissues The device 10 of this invention effectively provides vestibular stimulation and/or cranial nerve stimulation, and therefore direct brain tissue stimulation, in numerous embodiments that include combinations and sub-combinations of the various elements described above. It is entirely within the scope of the device for the ear insert to be used with or without the above-described sleeve 40, which in one embodiment is removable and disposable. Similarly, the device 10 may incorporate other features that assist in providing a diagnostic or therapeutic result. For example, certain applications may be optimized if the active elements of the device are in a particular position, and other applications may be optimized if the individual's head is in a particular position. For this situation, the device may include an inclinometer that measures the angle at which the individual's head is positioned in relation to a known norm. In a preferred embodiment, the device incorporates an incline indicator to show the individual or a health care provider the current angle at which an individual's head is positioned. Naturally, the inclinometer includes a calibration device to adjust for a particular individual's natural head position.

The devices disclosed herein incorporate standard features that are commonly used in hearing aids and other inner ear devices known today. For instance, given the fact that vestibular stimulation will likely not be administered around the clock, the device incorporates an automatic shutdown mode enabled during extensive periods of inactivity. Other useful features available for the device include battery operation and padding for the outer portion worn on the outer ear. The housing 50 for the computerized control module may be available in stylized and appropriately colored models to accommodate the tastes of the individual wearing it.

Nerve Stimulators

Nerve stimulators according to the present invention may be provided in a variety of forms. In some embodiments, a nerve stimulator may be configured in the form of a probe or an elongate probe. Such configurations have been developed for electrical nerve stimulation and are well known. Thus, nerve stimulation probes of the present invention can be configured as vagal nerve stimulation probes, trigeminal nerve stimulation probes, glossopharyngeal nerve stimulation probes, deep brain stimulation probes, motor cortex stimulation probes, peripheral nerve stimulation probes, brainstem stimulation probes, spinal cord stimulation probes, etc. Alternatively, a nerve stimulator according to the present invention may be configured to be insertable into the ear canal of a subject. Such a stimulator may conformably engage the subject's ear canal.

In some embodiments, the apparatus further comprises a heat transfer structure thermally coupled to a first side of the TED; and a temperature controlled medium thermally coupled to a second side of the TED so that the TED is thermally coupled between the heat transfer structure and the temperature controlled medium. The temperature controlled medium may be either one or more components of the device itself positioned between the TED and the tissue, or the tissue being treated by the device.

In one embodiment, a stimulator as described herein can be positioned in or adjacent a nerve (e.g., in fascia superior to and near the nerve), and then the TED(s) activated sufficiently to cool the nerve and inhibit transmission therein. Control systems for and surgical implantation of the stimulator can be carried out in accordance with known techniques, such as described in United States Patent Publication No. 2008/0243212, or variations thereof that will be apparent to those skilled in the art based on the present disclosure.

Another embodiment, a method of stimulating a nerve in a subject in need thereof, can be carried out by providing a stimulator as described herein positioned in or adjacent said nerve (e.g., in fascia superior to and near the nerve), and then activating the TED sufficiently to stimulate said nerve. The nerve may be a peripheral nerve causing pain in the subject, with the nerve thermally stimulated sufficiently to reduce or relieve that pain. Examples include occipital or trigeminal nerves in patients afflicted with occipital or trigeminal neuralgia. Control systems for and surgical implantation of the stimulator can be carried out in accordance with known techniques, such as described in U.S. Pat. No. 6,505,075, or variations thereof that will be apparent to those skilled in the art based on the present disclosure.

An advantage of the present invention is that, when nerve stimulation is delivered from a device of the present invention, either through a separate electrode or through one of the TEDs on the device (e.g., a first TED activated by an adjacent second TED, where the second TED is electrically activated to deliver a thermal stimulus, and the first TED is activated by that thermal stimulus to deliver an electrical stimulus to the patient or subject), one or more TEDs on the device can be used to deliver a local thermal stimulus to the patient tissue to alter the responsiveness of the patient or subject tissue to that electrical stimulus (e.g. heat to increase sensitivity to electrical stimulus; cool to decrease sensitivity to electrical stimulus).

Further examples of stimulators of the present invention are schematically illustrated on page 4 (FIGS. 1 and 2) of U.S. Provisional Application No. 61/224,668, the disclosure of which is incorporated herein by reference in its entirety.

Cochlear Implants

In some embodiments, a device of the present invention may be configured as a cochlear implant. Such an implant, or cochlear stimulator, may be configured to be inserted into the cochlea of a subject with the TEDs positioned in a (preferably linear) array to stimulate a plurality of ganglion cells in the basal region of the cochlea. In such an embodiment the array can be configured so that while one TED is activated to stimulate ganglion cells with heat, adjacent TEDs are activated to cool adjacent ganglion cells, thereby inhibiting undesired activation of adjacent ganglion cells. In such an embodiment, the adjacent TEDs can advantageously be thermally coupled to one another (e.g., by direct contact to one another, and/or through a thermal or heat transfer structure, which may be the support itself and/or a separate structure such as a heat sink) so that each at least partially offsets thermal energy displaced by the other. Such a cochlear implant or stimulator can be constructed with known elements and in accordance with known designs, modified to incorporate the TEDs as described herein. See, e.g., U.S. Pat. No. 6,038,484.

Concurrent Electrical Stimulation

In some embodiments, the probe can also include one or more electrodes that can be used to concurrently (e.g., sequentially or simultaneously) apply an electrical current to the tissue being stimulated. The electrodes can be separate from the TEDs, or the TEDs can themselves be utilized as electrodes. Where the TEDs are themselves used as electrodes (in addition to their use for heating or cooling the tissue), they can optionally be provided with separate or additional electrical lead lines for carrying the electrical stimulation signal.

Concurrent Hall Effect Stimulation

In some embodiments, the apparatus can further comprise: two magnetic coils of opposite polarity, each adapted to generate a magnetic field in a patient's tissue, the coils being positioned to generate a substantially toroidal magnetic field within the patient's tissue; and an ultrasound source adapted to transmit a focused ultrasound beam into the patient's tissue, as described in United States Patent Publication No. 2007/0255085, the disclosure of which is incorporated herein by reference. As with concurrent electrical stimulation, the Hall effect stimulation may be applied sequentially or simultaneously with the heating and/or cooling of the tissue being stimulated.

Concurrent Drug Delivery

In some embodiments, the apparatus can further comprise one or more reservoirs formed in or positioned in the probe, each reservoir positioned adjacent one or more TEDs. The reservoir can contain a pharmaceutical or active agent to be delivered to the tissue being stimulated, such as described in U.S. Pat. No. 6,178,349. The reservoir can be in any suitable form, including as a liquid-containing chamber, as a solid or semi-solid drug depot such as a thin film comprising the active agent in a carrier, etc. Heating or cooling of the reservoir is applied through an adjacent TED to speed or slow the release of active agent to the tissue.

Controllers and Systems

A device of the present invention is typically associated with a controller, which controller is in turn operatively associated with a power supply. The controller and power supply can be contained within the device (e.g., in an external housing), in a belt-worn or other housing, connected to a stationary unit such as a personal computer, or in any other suitable configuration. In a preferred embodiment, the controller includes a computerized control module programmed with computer instructions (i.e., software) that controls the magnitude, duration, wave pattern, and other attributes of the stimulation.

Once the device is positioned on or in the subject, the at least one thermoelectric transducer, each of which is operatively associated with the controller by a separate lead, is activated for a time and to a temperature sufficient to deliver CVS and/or nerve stimulation to the subject. An adjustable or programmable control module can be utilized to optimize stimulation for a particular subject, and for a particular purpose or condition. Where there are at least two separately controllable thermoelectric transducers on the device, the activating step can comprise separately and selectively activating the at least two separately controllable thermoelectric transducers (e.g., by activating only one or two thereof, by heating one transducer and cooling another; by sequentially activating transducers; by activating different transducers to different degrees; combinations of some or all of the foregoing, etc.). Patterns of separate and selective activation can be preprogrammed, can be determined empirically, can be optimized by the subject or a programmer (such as a clinician) in a programming session with the subject, etc.

Some embodiments of the invention comprise a stimulator system, the system comprising a stimulation probe as described above and a controller electrically coupled to the TED or devices of that probe, wherein the controller is configured to sense a first value of an electrical characteristic of the TED, to generate a first electrical control signal to pump heat through the TED in response to sensing the first value of the electrical characteristic of the TED, to sense a second value of the electrical characteristic of the TED wherein the first and second values of the electrical characteristic are different, and to generate a second electrical control signal to pump heat through the TED in response to sensing the second electrical characteristic of the TED, wherein the first and second electrical control signals are different.

Where multiple TEDs are included on the probe, the controller is preferably separately coupled to each TED so that each TED can be controlled separately and independently of one another, as noted above.

In some embodiments, the controller is configured to sense the first and second electrical characteristics by sensing electrical signals generated by the TED responsive to first and second heat gradients across the TED.

In some embodiments, the controller is configured to generate the first electrical control signal so that heat is pumped through the TED in a first direction, and to generate the second electrical control signal so that heat is pumped through the TED in a second direction opposite the first direction.

In some embodiments, the controller is configured to generate the first electrical control signal so that a first electrical current flows through the TED in a first direction, and to generate the second electrical control signal so that a second electrical current flows through the TED in a second direction opposite the first direction.

In some embodiments, the controller is configured to generate the first and second electrical control signals to maintain a stable temperature of the temperature controlled medium.

In some embodiments, the controller is configured to generate the first and second electrical control signals to provide a temperature ramp for the temperature controlled medium.

In some embodiments, the controller is configured to generate the first and second electrical control signals to provide a cyclical temperature profile for the temperature controlled medium.

Additional details of controllers useful for carrying out the present invention are described in U.S. patent application Ser. Nos. 11/972,267 and 12/166,953, the disclosures of which are incorporated by reference herein in their entirety.

The controller can be enclosed or sealed in a separate control module, which can be connected to the stimulator device with an elongate flexible lead. The control module can be an implantable module or can be worn externally by the subject.

Where the nerve stimulator is a cochlear implant the controller is correspondingly configured as cochlear implant controller for detecting auditory stimuli, such as speech or other sound, and stimulating ganglion cells in the basal region of the cochlea at the location corresponding to the frequency of the sound detected, so that the sound or speech can be perceived by the subject or subject, in accordance with known techniques (such as described in U.S. Pat. No. 6,259,951) or variations thereof that will be apparent to those skilled in the art.

Current Steering

In some embodiments, where multiple TEDs are included on the probe, the device can include a power steering capability for adjusting the power, signal, and/or timing of signal to particular TEDs on the probe. This is advantageous when, for example, the probe includes multiple TEDs thermally coupled to one another, and one or more TEDs are used to apply heat to tissue, and one or more TEDs are concurrently used to cool tissue, so that displaced heat is offset at least in part from one device to another. Current steering can be implemented in accordance with known techniques or variations thereof that will be apparent to those skilled in the art. See, e.g., U.S. Pat. No. 6,909,917, the disclosure of which is incorporated by reference herein in its entirety. Such a current steering unit or controller can include a pulse generator responsive to programming signals for generating stimulation currents; a system responsive to the programming signals for selectively applying the stimulation currents to one or more TEDs; and/or a current steering unit responsive to directional signals configured for steering the stimulation currents from the at least one first TED to at least one second TED. The current steering unit may optionally be configured to redistribute currents from the TEDs in a manner that is perceived as a smooth redistribution. The redistributing unit may optionally include a formula-based algorithm means for redistributing stimulation current from one of the electrodes included within the array of devices to another of the electrodes included within the array of devices. Preferably, the redistribution unit includes programming or an alogorithm to compare power or current routed to TEDs that are heating tissue and TEDs in thermal contact therewith that are cooling tissue, so that heat transfer can be at least partially offset therebetween.

Sensors.

In some embodiments, the system can further comprise a sensor for a subject (or patient) parameter, operatively associated with the at least one TED. The sensor may be associated with the TED in any suitable manner, such as by connection to a signal processor which is, in turn, operatively associated with the controller, so that the controller activates or inactivates the at least one TED as desired when a particular subject or patient parameter (e.g., a physical or physiological characteristic of the subject or patient) is detected.

Suitable sensors include, but are not limited to, motion detectors (discussed further below), blood pressure sensors, heart rate sensors, blood gas (e.g. oxygen, carbon dioxide) level sensors, electrocardiogram (ECG) sensors, electroencephalogram (EEG) sensors, electrooculogram (EOG) sensors, elecstronystagmography sensors, breathing or breath-rate sensors, nystagmus sensors, galvanic skin response (GSR) sensors, tympanic membrane temperature sensors, brain temperature sensors, local tissue temperature sensors or thermistors, etc. Numerous such sensors are known and can be operatively associated with the systems described herein in accordance with known techniques or variations thereof that will be apparent to those skilled in the art given the present disclosure. See, e.g., U.S. Pat. Nos. 7,578,793; 7,558,622; 7,396,330; 7,215,994; 7,197,357; 7,087,075; and 6,467,905, the disclosures of which are incorporated by reference herein in their entirety.

In some embodiments the sensor is mounted on or connected to the probe—for example, as can be the case of a tissue temperature sensor.

In some embodiments, the sensor is mounted in a separate housing—as can be the case for a motion detector.

In some embodiments, the sensor is applied separately to the subject, as can be the case for a GSR sensor.

Motion Detectors

In some embodiments, the system can further comprise a motion detector (e.g., an accelerometer) and a signal processor operatively associated with the motion detector. The signal process is in turn operatively associated with the controller, so that the controller activates the at least one TED as desired when a particular movement or motion is detected. For example, the signal processor can be configured to detect tremors, such as described in PCT Publication No. WO 2006/033039. In another example, the signal processor can be configured to perform a gait analysis, such as described in PCT Publication No. WO2007/088374; Lemke, *J. Psychiatric Research,* 34:277 (July 2000); Lee et al., *Spine* 32:1329 (May 2007); Neville and Boyd, *J. Neurol., Neurosurg, and Psychiatry,* 58:371 (1995); and Beauchet, *Neuropsychiatric Disease and Treatment* 4:155 (2008). The gait analysis can be one which detects a gait associated with a particular neurological disorder and activates the at least one TED when a gait associated with that neurological disorder is detected.

In addition to activating the at least one TED, the motion detector can further be configured to monitor the subject for the cessation of the particular motion or gait and the controller then configured to deactivate the at least one TED once that motion or gait has ceased.

The MMA7660FC 3-Axis Orientation/Motion Detection Sensor, commercially available from Freescale Semiconductor, Inc. (Austin, Tex.), is one example of a suitable motion detector.

The motion detector can be positioned in the probe itself, in the control module, or positioned anywhere on the subject suitable for motion detection.

Sensors and Controllers.

Figure 21:
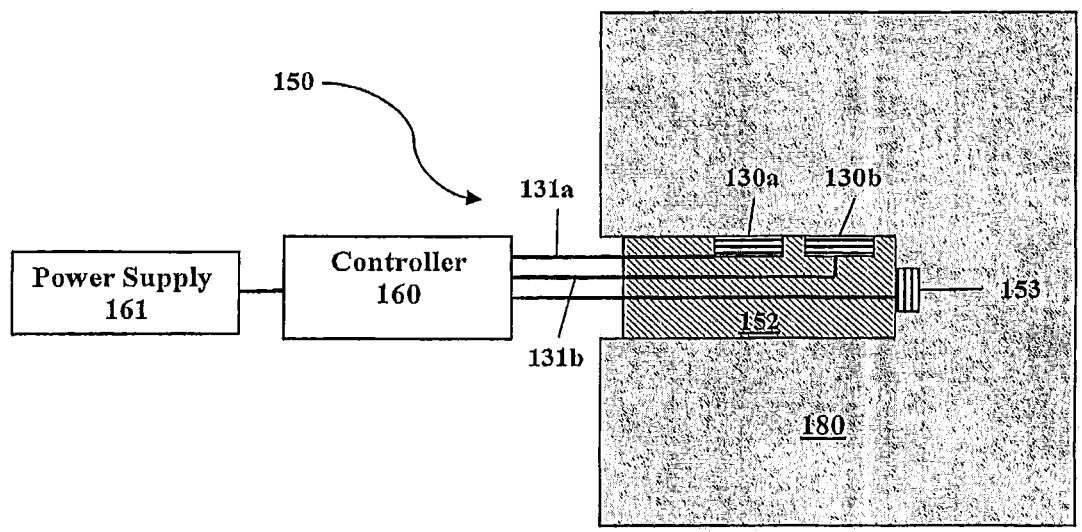
FIG. 21 is a schematic illustration of an apparatus of the invention operatively associated with a power supply, controller, and a tissue temperature sensor.
Figure 22:
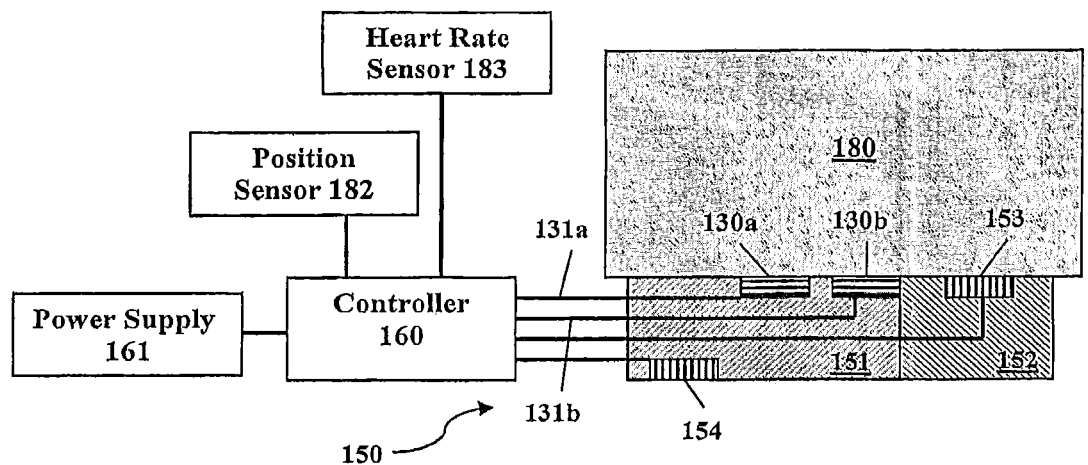
FIG. 22 is a schematic illustration of an apparatus of the invention operatively associated with a power supply, controller, tissue temperature sensor, heat sink temperature sensor, and patient position sensor.

FIGS. 21-22 schematically illustrate stimulators 150 of the present invention operatively associated with a controller 160, which controller is in turn operatively associated with a power supply 161. The controller 160 and power supply 161 can be contained within the device (e.g., in an external housing 50 as described in connection with FIGS. 13-14 above), in a belt-worn or other housing, connected to a stationary unit such as a personal computer, or in any other suitable configuration. In some embodiments the stimulator may comprise a heat-sink 151 formed of a thermally conductive material such as aluminum, and may include an additional element of thermally insulating material (e.g., an organic polymer material) 152 connected thereto for carrying a sensor such as a tissue or patient temperature sensor 153. Additional sensors such as a heart rate sensor 183 or patient position sensor 182 can be included as desired depending upon the particular configuration of the device and purpose for which the device is being used. For example, the optimum patient position for administering CVS is a reclining position of about 30 degrees, and a position sensor can be included to automatically activate the thermoelectric devices once such a position is achieved.

A temperature sensor 154 may be associated with the heat sink for adjusting or modulating the thermoelectric devices, e.g., if a predetermined low or high temperature of the heatsink is detected (e.g., inactivating the thermoelectric devices when a predetermined high temperature of the heatsink is detected when the thermoelectric devices are being activated to cool tissue). In a preferred embodiment, the controller is configured (e.g., with computer instructions (i.e., software) that controls or adjusts the magnitude, duration, wave pattern, and other attributes of the stimulation, in response to signals received from the various sensors associated therewith.

As shown in FIGS. 21 and 22, once the device is positioned in or on the subject, 180 (e.g., within the ear canal of a subject, or in or adjacent nerve tissue of the subject), the at least one thermoelectric transducer 130a, 130b, each of which is operatively associated with the controller by a separate lead 131a, 131b, is controlled activated for a time and to a temperature sufficient to deliver stimulation to the subject (e.g. CVS and/or cranial nerve stimulation). An adjustable or programmable control module can be utilized to optimize stimulation for a particular subject, and for a particular purpose or condition. Where (as shown in FIGS. 21-22) there are at least two separately controllable thermoelectric transducers on the device spaced apart from one another, the activating step can comprise separately and selectively controlling or adjusting (e.g., activating, modulating, adjusting) the at least two separately controllable thermoelectric transducers (e.g., by activating only one or two thereof, by heating one transducer and cooling another; by sequentially activating transducers; by activating different transducers to different degrees; combinations of some or all of the foregoing, etc.) Patterns of separate and selective activation can be preprogrammed, can be determined empirically, can be optimized by the subject or a programmer (such as a clinician) in a programming session with the subject, etc.

Stimulation Signal

Any suitable stimulation signal can be utilized, including but not limited to continuous stimulation and cyclic stimulation (e.g., heat then off and repeat; cool then off and repeat; heat then cool and repeat, cool then heat and repeat, cool then off then heat and repeat, etc.) which cyclic stimulation may produce different types of waveforms, such as uniform, randomized/stochastic, etc.

In some embodiments, the TED is configured to provide thermal pulses. Such thermal pulses may be warming pulses or cooling pulses. Thermal pulses of the present invention may be from about one-half second to about ten minutes in duration, with each pulse being separated in time by about one-half second to about 12 hours. In some such embodiments, the thermal pulses are about one-half second to about two seconds in duration and are separated by intervals of about one-half second to about ten seconds. In other embodiments, the thermal pulses are about two to about ten seconds in duration and are separated by intervals of about ten to about thirty seconds. In further embodiments, the thermal pulses are about ten seconds to about two minutes in duration and are separated by intervals of about one to about five minutes. In still further embodiments, the thermal pulses are about 30 seconds in duration and are separated by intervals of about 3 to about 5 minutes. In yet further embodiments, the thermal pulses are about 10 minutes in duration and are separated by intervals of about 1 to about 12 hours.

The magnitude of the thermal stimulus delivered via TED activation will depend upon factors such as the tissue being stimulated, the volume of tissue being stimulated, the intensity and/or duration of the stimulus, the condition of the subject, and the particular diagnosis or treatment.

In some embodiments, for cooling, the tissue immediately or most closely adjacent the TED is cooled at least 1, 2, 3, or 4 degrees Centigrade, up to 5, 10 or 20 degrees Centigrade, or more. In some embodiments, the tissue immediately or most closely adjacent the TED is cooled by about 0.5 degree to about 37 degrees Centigrade. In some embodiments, the tissue immediately or most closely adjacent the TED is cooled by about 7 to about 33 degrees Centigrade, preferably by about 17 to about 27 degrees Centigrade. In some embodiments, the ear canal of a subject is cooled by about 0.5 degree to about 37 degrees Centigrade. In some embodiments, the ear canal of a subject is cooled by about 7 to about 33 degrees Centigrade, preferably by about 17 to about 27 degrees Centigrade. Those skilled in the art will appreciate how to select appropriate limits on the intensity/duration of stimulation and/or the volume of tissue being thermally treated to avoid tissue damage.

In some embodiments, for heating, the tissue immediately adjacent or most closely adjacent the TED is heated at least 1, 2, 3, or 4 degrees Centigrade, up to 5, 10 or 20 degrees Centigrade, or more. In some embodiments, the tissue immediately or most closely adjacent the TED is heated by about 0.5 degree to about 11 degrees Centigrade. In some embodiments, the tissue immediately or most closely adjacent the TED is warmed by about 0.5 degree to about 6.5 degrees Centigrade, preferably by about 2 to about 4 degrees Centigrade. In some embodiments, the ear canal of a subject is heated by about 0.5 degree to about 11 degrees Centigrade. In some embodiments, the ear canal of a subject is warmed by about 0.5 degree to about 6.5 degrees Centigrade, preferably by about 2 to about 4 degrees Centigrade. Those skilled in the art will appreciate how to select appropriate limits on intensity/duration of stimulation and/or the volume of tissue being thermally treated to avoid tissue damage.

In some embodiments, the TED is activated for a period of about 1 to about 20 minutes, preferably for about 5 to about 10 minutes.

In a preferred embodiment, a device of the present invention (having a conical metal (e.g., medical grade aluminum) probe for insertion into the ear, which probe is cooled by a thermoelectric device contacting the probe external to the ear and an outer housing therefore) is inserted into the ear canal of a subject, and the TED is activated sufficient to cool the ear canal of the subject by about 17 degrees for a period of about 7.5 minutes. Such an embodiment is used to treat a subject suffering from a migraine headache.

Where multiple TEDs are incorporated into a single stimulator, different modes and patterns of stimulus can be applied through each TED (some of the TEDs may be utilized to heat while others are utilized to cool; some of the TEDs may be utilized while others are not; some of the TEDs may be utilized to electrically stimulate tissues while others are utilized to thermally stimulate (heat and/or cool) the tissue, etc.). Non-limiting examples are set forth in Table 3.

TABLE 3

Exemplary stimulation patterns for apparatuses incorporating multiple TEDs

| TEC #1 | TEC #2 | TEC #3 |
|---|---|---|
| 1. Cool | Cool | Cool |
| 2. Heat | Heat | Heat |
| 3. Electric current | Heat | |
| 4. Electric current | Cool | |
| 5. Stochastic-electric | Cool | |
| 6. Stochastic-electric | Heat | |
| 7. Stochastic-heat | Heat | |
| 8. Stochastic-cool | Cool | |
| 9. Stochastic-cool | Cooling waveform | |
| 10. Stochastic-heat | Heat waveforms (sinusoidal, square sawtooth) | |
| 11. Stochastic-electric | Electric waveforms | |
| 12. Combinations | | |
| 13. Delivery of thermal or electric stimulus via hydrogel | | |
| 14. Delivery of electrical stimulus across cultured neuronal tissues | | |

Combination Treatment

Tissue stimulators, probes, systems and apparatuses of the invention can be used alone or in combination with other control and/or stimulation elements, provided on the same probes and in the same controllers or on separate stimulators and/or controllers to achieve a combined treatment effect through multiple modes of stimulation. Additional modes of stimuli include, but are not limited to, those described in U.S. Pat. Nos. 5,571,150; 5,922,016; 5,643,330; 6,341,236; 6,699,269; 5,529,574; 5,707,367; 7,232,458; 6,486,059; 6,735,475; 6,526,318; etc.

Similarly, stimulators, probes, systems and apparatuses of the present invention may be used in combination with pharmaceuticals, physical therapy, psychological and other counseling, etc. to achieve a combined treatment effect. One skilled in the art will appreciate how to select, combine and administer such pharmaceuticals and other treatment options.

Methods of Treatment and/or Diagnosis

An aspect of the invention is a method of treating a disorder in a subject in need thereof, comprising (i) positioning a thermoelectric device ("TED") in the ear canal of a subject and (ii) activating the TED sufficient to treat the disorder. Activating the thermoelectric device may comprise stimulating the vestibular system and/or at least one cranial nerve effective to treat the disorder. The disorder may include, but is not limited to, migraine headaches, asthma, Parkinson's disease, epilepsy, stroke, cellular ischemia, excitotoxic brain injury, traumatic brain injury, spinal cord injury, sensory disorders, motor disorders, and cognitive disorders.

In some embodiments, the disorder is selected from the group consisting of migraine headaches, neuropathic pain, body image or integrity disorders, visual intrusive imagery, depression, bipolar disorder, Parkinson's disease, epilepsy and other seizures, dementia, acute brain injury and insomnia.

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Activating the thermoelectric device may comprise stimulating the vestibular system and/or at least one cranial nerve effective to treat the disorder.

In some embodiments, the TED is activated sufficient to stimulate the subject's vestibular system, thereby resulting in treatment of the disorder.

In some embodiments, the TED is activated sufficient to treat the disorder without stimulating the subject's vestibular system. In some such embodiments, the disorder is treated by activating the TED such that it stimulates at least one cranial nerve without concurrently stimulating the vestibular system. The at least one cranial nerve may be selected from the group consisting of the vagus nerve, the trigeminal nerve, and the glossopharyngeal nerve.

In some embodiments, the disorder is treated by activating the TED sufficient to stimulate both the vestibular system and at least one cranial nerve of the subject (in addition to the vestibulocochlear nerve). In some such embodiments, the at least one cranial nerve is selected from the group consisting of the vagus nerve, the trigeminal nerve, and the glossopharyngeal nerve. Such activation may give rise to a beneficial synergy between the effects of vestibular stimulation and cranial nerve stimulation. In such embodiments, the at least one cranial nerve (other than the vestibulocochlear nerve) may be stimulated prior to CVS, following CVS, or concurrently with CVS.

In some embodiments, activating the TED sufficient to treat the disorder comprises warming the ear canal of the subject. In such embodiments, the ear canal is warmed by about 0.5 degree to about 11 degrees Centigrade. In some embodiments, the ear canal is warmed by about 0.5 degree to about 6.5 degrees Centigrade, preferably about 2 to about 4 degrees Centigrade. Those skilled in the art will appreciate how to select appropriate limits on duration/magnitude of stimulus to avoid tissue damage.

In some embodiments, activating the TED sufficient to treat the disorder comprises cooling the ear canal of the subject. In such embodiments, the ear canal is cooled by about 0.5 degree to about 37 degrees Centigrade. In some embodiments, the ear canal is cooled by about 7 to about 33 degrees Centigrade, preferably about 17 to about 27 degrees Centigrade. Those skilled in the art will appreciate how to select appropriate limits on duration/magnitude of stimulus to avoid tissue damage.

In some embodiments, activating the TED sufficient to treat the disorder comprises both warming and cooling the ear canal of the subject. In such embodiments, the ear canal may first be cooled then warmed, warmed then cooled, or cycled between warm and cool temperatures. The ear canal may be allowed to return to or near ambient temperature between such warming and cooling steps.

In some embodiments, the ear canal is cooled by about 0.5 degree to about 37 degrees Centigrade, and then warmed by about 0.5 to about 11 degrees Centigrade. In some embodiments, the ear canal is cooled by about 7 to about 33 degrees Centigrade, and then warmed by about 0.5 degree to about 6.5 degrees Centigrade. In some embodiments, the ear canal is cooled by about 17 to about 27 degrees Centigrade, and then warmed by about 2 to about 4 degrees Centigrade. Those skilled in the art will appreciate how to select appropriate limits on duration/magnitude of stimulus to avoid tissue damage.

In some embodiments, the ear canal is warmed by about 0.5 to about 11 degrees Centigrade, and then cooled by about 0.5 degree to about 37 degrees Centigrade. In some embodiments, the ear canal is warmed by about 0.5 degree to about 6.5 degrees Centigrade, and then cooled by about 7 to about 33 degrees Centigrade. In some embodiments, the ear canal is warmed by about 2 to about 4 degrees Centigrade, and then cooled by about 17 to about 27 degrees Centigrade. Those skilled in the art will appreciate how to select appropriate limits on duration/magnitude of stimulus to avoid tissue damage.

A further aspect of the present invention is a method of treating migraine headaches in a subject in need thereof, comprising (i) positioning a TED in the ear canal of a subject, and (ii) activating the TED sufficient to treat the migraine headache.

Activating the thermoelectric device may comprise stimulating the vestibular system and/or at least one cranial nerve effective to treat the migraine headache.

In some embodiments, the TED is activated sufficient to stimulate the subject's vestibular system, thereby resulting in treatment of the migraine headache.

In some embodiments, the TED is activated sufficient to treat the migraine headache without stimulating the subject's vestibular system. In some such embodiments, the migraine headache is treated by activating the TED such that it stimulates at least one cranial nerve without concurrently stimulating the vestibular system. The at least one cranial nerve may be selected from the group consisting of the vagus nerve, the trigeminal nerve, and the glossopharyngeal nerve.

In some embodiments, the migraine headache is treated by activating the TED sufficient to stimulate both the vestibular system and at least one cranial nerve of the subject (in addition to the vestibulocochlear nerve). In some such embodiments, the at least one cranial nerve is selected from the group consisting of the vagus nerve, the trigeminal nerve, and the glossopharyngeal nerve. Such activation may give rise to a beneficial synergy between the effects of vestibular stimulation and cranial nerve stimulation. In such embodiments, the at least one cranial nerve (other than the vestibulocochlear nerve) may be stimulated prior to CVS, following CVS, or concurrently with CVS.

In some embodiments, activating the TED sufficient to treat the migraine headaches comprises warming the ear canal of the subject by about 0.5 degree to about 11 degrees Centigrade. In some embodiments, the ear canal is warmed by about 0.5 degree to about 6.5 degrees Centigrade, preferably about 2 to about 4 degrees Centigrade. Those skilled in the art will appreciate how to select appropriate limits on duration/magnitude of stimulus to avoid tissue damage.

In some embodiments, activating the TED sufficient to treat the migraine headaches comprises cooling the ear canal of the subject by about 0.5 degree to about 37 degrees Centigrade. In some embodiments, the ear canal is cooled by about 7 to about 33 degrees Centigrade, preferably about 17 to about 27 degrees Centigrade. Those skilled in the art will appreciate how to select appropriate limits on duration/magnitude of stimulus to avoid tissue damage.

In some embodiments, activating the TED sufficient to treat the migraine headache comprises both warming and cooling the ear canal of the subject. In such embodiments, the ear canal of the subject may first be cooled then warmed, warmed then cooled, or cycled between warm and cool temperatures. The ear canal may be allowed to return to or near ambient temperature between such warming and cooling steps.

In some embodiments, the ear canal is cooled by about 0.5 degree to about 37 degrees Centigrade, and then warmed by about 0.5 to about 11 degrees Centigrade. In some embodiments, the ear canal is cooled by about 7 to about 33 degrees Centigrade, and then warmed by about 0.5 degree to about 6.5 degrees Centigrade. In some embodiments, the ear canal is cooled by about 17 to about 27 degrees Centigrade, and then warmed by about 2 to about 4 degrees Centigrade. Those skilled in the art will appreciate how to select appropriate limits on duration/magnitude of stimulus to avoid tissue damage.

In some embodiments, the ear canal is warmed by about 0.5 to about 11 degrees Centigrade, and then cooled by about 0.5 degree to about 37 degrees Centigrade. In some embodiments, the ear canal is warmed by about 0.5 degree to about 6.5 degrees Centigrade, and then cooled by about 7 to about 33 degrees Centigrade. In some embodiments, the ear canal is warmed by about 2 to about 4 degrees Centigrade, and then cooled by about 17 to about 27 degrees Centigrade. Those skilled in the art will appreciate how to select appropriate limits on duration/magnitude of stimulus to avoid tissue damage.

A still further aspect of the present invention is a method of stimulating cognitive enhancement and/or neuroprotection in a subject. Such cognitive enhancement may comprise enhanced memory function (including, but not limited to, spatial and verbal memory), enhanced cognitive reserves, increases in attentive capacity, lessened anxiety, increased motivation, etc.

In some embodiments, cognitive enhancement and/or neuroprotection is stimulated in a subject experiencing mental and/or physical stress, such as that caused by prolonged sleep deprivation, prolonged periods of intense mental and/or physical exertion, etc. Such stimulation may be administered prior to, concurrently with, or after the subject experiences said mental and/or physical stress.

In some embodiments, cognitive enhancement and/or neuroprotection is stimulated in a subject prior to said subject receiving general and/or local anesthetic. Such stimulation may be useful prior to said subject receiving anesthetic as part of a surgical procedure which relates to the brain and/or the nervous system. Stimulating the brain in advance of neurological surgery may be particularly useful.

In some embodiments, cognitive enhancement and/or neuroprotection is stimulated in a subject demonstrating indicators of declining cognitive function. Such indicators may include, but are not limited to, early signs of dementia, language deficiencies, rapid mood swings, personality changes, etc.

In some embodiments, cognitive enhancement and/or neuroprotection is stimulated in a subject who is suffering from or has recently suffered a potential cardiac infarction and/or stroke.

In some embodiments, cognitive enhancement and/or neuroprotection is stimulated in a subject that is about to undertake an activity and/or action for which cognitive ability and/or capacity is important.

In some embodiments, cognitive enhancement and/or neuroprotection is stimulated in a subject that is about to enter an environment which may have a negative effect on cognitive ability and/or capacity.

A further aspect of the present invention is a method of evaluating brain function in a test subject, comprising (i) stimulating the subject's vestibular system with a thermoelectric device, and (ii) determining whether the subject exhibits horizontal nystagmus.

A further aspect of the present invention is an improvement on a method of diagnosing a disorder and/or evaluating brain function in a test subject by creating an image of at least a portion of the brain of said test subject. The image may be, but is not limited to, a magnetic resonance imaging image (MRI), a functional magnetic resonance image (fMRI), an X-ray computed tomography (CT) image, an ultrasound image, a single photon emission computed tomography (SPECT) image, a positron emission tomography (PET) image, an electroencephalography (EEG) image or a magnoencephalography (MEG) image. Such diagnostic and imaging methods are well known in the art. See, e.g., Benveniste et al., PNAS USA 96:14079 (1999); see also U.S. Pat. Nos. 6,821,504, 7,333,845 and 7,469,159, the disclosure of each of which is incorporated herein by reference in its entirety. The improvement comprises stimulating the test subject's vestibular system with a thermoelectric device prior to or concurrently with creating said image.

In some embodiments, the method further comprises analyzing brain activity in one or more areas of the test subject's brain following stimulation of the test subject's vestibular system. Such brain activity may be compared to that of a healthy control subject who likewise received caloric vestibular stimulation or to the brain activity observed in an image of the test subject's brain that was taken during a previous testing session in which the test subject's vestibular system was stimulated.

Diagnostics Involving More than Determining Whether Brain Function Exists

Many disorders are centered within one side of the brain. Depression, for example, can reflect hyper-cortical activity or over-stimulation within the right side of the brain. This out-of-balance condition can be identified through imaging or through comparing the temperatures of the two sides of the brain. Since directly measuring the temperature within the brain is not practicable, a surrogate approach involves the use of Tympanic Membrane Thermometry (TMT).

Cortical hemispheric activity can be assessed using advanced imaging technologies. Elsewhere in this application we define the various imaging approaches which are available and which increasingly are used. A simpler approach can be facilitated using TMT. The following scheme reflects the practical application using the TNM device.

Thermal monitoring can occur in one or both ears, depending on the monitoring intent, with the TMT thermal monitor being placed at the tip of the ear canal insert in order to measure temperature within the brain on one or both sides. The core premise of thermal monitoring of hemispheric function is that the hemisphere which is experiencing excess activity will have a lower comparative temperature than does the other hemisphere because the excess cortical activity causes increased blood flow and that blood flow essentially acts as a heat sink and dissipates heat from that hemisphere.

Additionally, if that hemisphere is stimulated further, the associated ear canal temperature on the same side will fall further, and the differential side to side will increase further. If the other hemisphere is stimulated, the response in decreasing the temperature differential will not be as great and will not last as long as would be the case for an individual who does not have hemispherical cortical dysfunction.

Alternatively, imaging can be used to assess cortical activity within the two hemispheres and make these comparisons.

TNM Device: A device of the present invention can be provided with a thermal monitor in a single or both ears. Each hemisphere is activated sequentially through a specific task or through CVS, with concurrent measurement of ear canal temperature change from the baseline state. The drop in ear canal temperature reflects hemispheric activation. A larger differential indicates a greater likelihood that a disorder is causing excess cortical activity on one side of the brain. Using depression as an example: Depression can have associated right hemisphere preponderance. CVS activation of the right hemisphere via warming the right ear or cooling the left can result in a temperature decrease that is larger than the normal population would experience. It is also anticipated that such temperature decrease within the right hemisphere, and therefore the larger differential side-to-side, can be abnormally prolonged due to the hemispheric dysfunction.

Thus, for a given hemispheric-based disorder, several potential comparative tympanic membrane temperature states may exist, and the level of cortical activity and consequent temperature delta hemisphere-to-hemisphere will be increased when CVS is applied.

1. Normal tympanic temperature reduction (early disease)
2. Moderate temperature decrease with moderate CVS response
3. Significant baseline temperature decrease with further reduction via CVS (prolonged return to baseline)

CVS thus functions as a stress test for the propensity of cerebral hemisphere activation to shift ear temperatures in a negative direction.

The depression example is readily applicable to any disorder with hemispheric dysfunction or propensity.

As noted above, imaging rather than temperature measurements can be used for the assessments.

CVS can also be used to diagnose hemispheric dysfunction by assessing the strength of response to stimulation through measurement of nystagmus. See, e.g., A. Soza Ried and M. Aviles, *Neuroscience* 144, 128-134 (2007).

The foregoing is illustrative of the present invention, and is not to be construed as limiting thereof. The invention is defined by the following claims, with equivalents of the claims to be included herein.

That which is claimed:

1. A device comprising:
    an ear insert sized and configured so as to be at least partially insertable into a subject's ear canal;
    a thermoelectric device (TED) attached to said ear insert;
    a heat sink; and
    a controller configured to control said TED and receive a sensor signal from a sensor,
    wherein said TED is thermally coupled between said ear insert and said heat sink, and
    wherein said controller is operatively connected to said TED and is configured to activate said TED so as to produce a thermal stimulus responsive to the sensor signal,
    wherein said sensor signal comprises a signal from a sensor selected from the group consisting of position sensors, motion detectors, blood pressure sensors, heart rate sensors, blood gas level sensors, electrocardiogram (ECG) sensors, electroencephalogram (EEG) sensors, electrooculogram (EOG) sensors, electronystagmography sensors, breath-rate sensors, nystagmus sensors, galvanic skin response (GSR) sensors, tympanic membrane temperature sensors, brain temperature sensors, and tissue temperature sensors.

2. The device of claim 1, wherein said sensor signal comprises a signal from a tissue temperature sensor, and said controller is configured to adjust said thermal stimulus in response to said sensor signal.

3. The device of claim 1, wherein said sensor signal comprises a signal from a galvanic skin response (GSR) sensor, and said device further comprises an electrode attached to said ear insert and operatively connected to said controller,
    wherein said controller is configured to activate said electrode so as to produce an electrical stimulus.

4. The device of claim 3, wherein said controller is configured to control the magnitude, duration and/or waveform of said electrical stimulus by modulating activation of said electrode.

5. The device of claim 3, further comprising a sensor that is operatively connected to said controller, wherein said controller is configured to control activation of said TED and/or activation of said electrode responsive to feedback received from said sensor.

6. The device of claim 3, wherein said controller is configured to separately and selectively activate said TED and said electrode.

7. The device of claim 1, wherein said TED comprises a thin film thermoelectric transducer.

8. The device of claim 1, wherein said heat sink is configured on said device for positioning outside the ear canal of said subject.

9. The device of claim 1, wherein said controller is configured to control the magnitude, duration and/or waveform of said thermal stimulus by modulating activation of said TED.

10. The device of claim 1, wherein said controller is configured to cyclically activate said TED.

11. The device of claim 1, wherein said controller is configured to activate said TED so as to produce the thermal stimulus comprising a uniform waveform.

12. The device of claim 1, wherein said controller is configured to activate said TED so as to produce the thermal stimulus comprising a stochastic waveform.

13. The device of claim 1, wherein said controller is configured to activate said TED so as to produce the thermal stimulus comprising a randomized waveform.

14. The device of claim 1, wherein said controller is configured to activate said TED so as to produce the thermal stimulus comprising one or more thermal pulses.

15. The device of claim 1, wherein said controller is configured to activate said TED so as to produce the thermal stimulus comprising a cooling thermal stimulus, a warming stimulus or combinations thereof.

16. A method, comprising:
    providing a device comprising:
        an ear insert sized and configured so as to be at least partially insertable into a subject's ear canal;
        a thermoelectric device (TED) attached to said ear insert;
        a heat sink; and
        a controller,
        wherein said TED is thermally coupled between said ear insert and said heat sink, and
        wherein said controller is operatively connected to said TED and is configured to activate said TED so as to produce a thermal stimulus;
    inserting at least a portion of said ear insert into the ear canal of a subject;
    activating said TED,
    wherein said thermal stimulus is configured to treat a disorder in a patient in need of treatment thereof.

17. The method of claim 16, wherein said disorder is headache.

18. The method of claim 17, wherein said disorder is migraine headache.

19. The method of claim 16, wherein said disorder is Parkinson's disease.

20. The method of claim 16, wherein said disorder is Alzheimer's disease.

21. The method of claim 16, wherein said disorder is selected from the group consisting of epilepsy, stroke, cellular ischemia, excitotoxic brain injury, traumatic brain injury, spinal cord injury, sensory disorders, motor disorders, and cognitive disorders.

\* \* \* \* \*